US010448956B2

(12) United States Patent
Gordon et al.

(10) Patent No.: US 10,448,956 B2
(45) Date of Patent: Oct. 22, 2019

(54) COMPUTER-ASSISTED PLANNING AND EXECUTION SYSTEM

(71) Applicants: THE JOHNS HOPKINS UNIVERSITY, Baltimore, MD (US); THE UNITED STATES OF AMERICA AS REPRESENTED BY THE SECRETARY OF THE NAVY, Arlington, VA (US); THE UNITED STATES OF AMERICA AS REPRESENTED BY THE SECRETARY OF DEFENSE, Bethesda, MD (US)

(72) Inventors: Chad Gordon, Lutherville, MD (US); Mehran Armand, Fulton, MD (US); Ryan Murphy, Columbia, MD (US); Gerald Grant, Goshen, KY (US); Peter Liacouras, North Potomac, MD (US); Kevin Wolfe, Lutherville, MD (US); Ehsan Basafa, Baltimore, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 294 days.

(21) Appl. No.: 15/100,215

(22) PCT Filed: Nov. 26, 2014

(86) PCT No.: PCT/US2014/067671
§ 371 (c)(1),
(2) Date: May 27, 2016

(87) PCT Pub. No.: WO2015/081232
PCT Pub. Date: Jun. 4, 2015

(65) Prior Publication Data
US 2017/0000564 A1    Jan. 5, 2017

Related U.S. Application Data

(60) Provisional application No. 62/049,866, filed on Sep. 12, 2014, provisional application No. 61/940,196, (Continued)

(51) Int. Cl.
*A61B 5/02* (2006.01)
*A61B 17/15* (2006.01)
(Continued)

(52) U.S. Cl.
CPC .......... *A61B 17/15* (2013.01); *A61B 17/1695* (2013.01); *A61B 17/176* (2013.01); (Continued)

(58) Field of Classification Search
CPC ................... A61B 2034/108; A61B 2034/101 (Continued)

(56) References Cited

U.S. PATENT DOCUMENTS 3,457,922 A    7/1969  Ray
4,436,684 A    3/1984  White
(Continued)

FOREIGN PATENT DOCUMENTS

WO    2012147114 A1    11/2012
WO    2013101753 A1    7/2013

OTHER PUBLICATIONS

Written Opinion and International Search Report dated Mar. 9, 2015 from corresponding International Application No. PCT/US2014/067671; 13 pages.
(Continued)

*Primary Examiner* — Thomas J Lett
(74) *Attorney, Agent, or Firm* — MH2 TECHNOLOGY LAW GROUP, LLP

(57) ABSTRACT

A method for computer-assisted planning of a transplant surgery is provided. The method includes obtaining a com-
(Continued)

puter-readable representation of a donor and recipient skeletal fragment; determining surgical cutting planes on the computer-readable representation of the donor skeletal fragment from which a portion of the donor skeletal fragment from the computer-readable representation of the donor skeletal fragment will be harvested; determining virtual cutting guides; performing a virtual osteotomy to separate the portion of the donor skeletal fragment from the computer-readable representation of the donor skeletal fragment from a remainder portion of the donor skeletal fragment based on a position of the virtual cutting guides that are attached to the computer-readable representation of the donor skeletal fragment; positioning the donor skeletal fragment within a transplant region of the recipient skeletal fragment; and creating a hybrid computer-readable representation comprising the recipient skeletal fragment and the portion of the donor skeletal.

13 Claims, 20 Drawing Sheets

Related U.S. Application Data filed on Feb. 14, 2014, provisional application No. 61/910,204, filed on Nov. 29, 2013.

(51) Int. Cl.

| | |
|---|---|
| *G16H 50/50* | (2018.01) |
| *A61B 17/17* | (2006.01) |
| *A61B 34/10* | (2016.01) |
| *A61B 34/20* | (2016.01) |
| *A61B 17/16* | (2006.01) |
| *A61B 17/80* | (2006.01) |
| *A61F 2/28* | (2006.01) |
| *G06F 19/00* | (2018.01) |

(52) U.S. Cl.
CPC ...... *A61B 17/1739* (2013.01); *A61B 17/8085* (2013.01); *A61B 34/10* (2016.02); *A61B 34/20* (2016.02); *A61F 2/2803* (2013.01); *G06F 19/00* (2013.01); *G06F 19/3481* (2013.01); *G16H 50/50* (2018.01); *A61B 2034/105* (2016.02); *A61B 2034/108* (2016.02); *A61B 2034/2051* (2016.02); *A61B 2034/2055* (2016.02); *A61B 2034/2065* (2016.02); *Y02A 90/26* (2018.01)

(58) Field of Classification Search
USPC .......................................................... 345/420
See application file for complete search history.

(56) References Cited

U.S. PATENT DOCUMENTS

| | | | |
|---|---|---|---|
| 5,279,575 | A | 1/1994 | Sugarbaker |
| 5,741,215 | A | 4/1998 | DUrso |
| 5,810,712 | A | 9/1998 | Dunn |
| 6,079,681 | A | 6/2000 | Stern et al. |
| 6,112,109 | A | 8/2000 | DUrso |
| 6,120,290 | A | 9/2000 | Fukushima et al. |
| 6,226,548 | B1 | 5/2001 | Foley et al. |
| 6,254,639 | B1 | 7/2001 | Peckitt |
| 6,285,902 | B1 | 9/2001 | Kienzle, III et al. |
| 6,491,699 | B1 | 12/2002 | Henderson et al. |
| 6,500,179 | B1 | 12/2002 | Masini |
| 6,608,628 | B1 | 8/2003 | Ross et al. |
| 6,726,678 | B1 | 4/2004 | Nelson et al. |
| 6,796,986 | B2 | 9/2004 | Duffner |
| 6,845,175 | B2 | 1/2005 | Kopelman et al. |
| 6,932,842 | B1 | 8/2005 | Litschko et al. |
| 7,050,877 | B2 | 5/2006 | Iseki et al. |
| 7,113,841 | B2 | 9/2006 | Abe et al. |
| 7,510,557 | B1 | 3/2009 | Bonutti |
| 7,596,399 | B2 | 9/2009 | Singhal et al. |
| 7,747,305 | B2 | 6/2010 | Dean et al. |
| 7,747,318 | B2 | 6/2010 | John et al. |
| 7,792,341 | B2 | 9/2010 | Schutyser |
| 7,857,821 | B2 | 12/2010 | Couture et al. |
| 7,953,260 | B2 | 5/2011 | Weinzweig et al. |
| 8,086,336 | B2 | 12/2011 | Christensen |
| 8,096,997 | B2 | 1/2012 | Plaskos et al. |
| 8,221,430 | B2 | 7/2012 | Park et al. |
| 8,221,461 | B2 | 7/2012 | Kuiper et al. |
| 8,357,165 | B2 | 1/2013 | Grant et al. |
| 8,397,732 | B2 | 3/2013 | Singhal et al. |
| 8,403,934 | B2 | 3/2013 | Angibaud et al. |
| 8,428,315 | B2 | 4/2013 | Suetens et al. |
| 8,518,085 | B2 | 8/2013 | Winslow et al. |
| 8,535,063 | B1 | 9/2013 | Amato |
| 8,650,005 | B2 | 2/2014 | Liao |
| 8,706,285 | B2 | 4/2014 | Narainasamy et al. |
| 8,781,557 | B2 | 7/2014 | Dean et al. |
| 9,208,558 | B2 | 12/2015 | Dean et al. |
| 9,216,084 | B2 | 12/2015 | Gordon et al. |
| 9,330,206 | B2 | 5/2016 | Dean et al. |
| 9,659,152 | B2 | 5/2017 | Mueller |
| 2001/0021851 | A1 | 9/2001 | Eberlein et al. |
| 2002/0035458 | A1 | 3/2002 | Kim et al. |
| 2002/0165552 | A1 | 11/2002 | Duffner |
| 2004/0091845 | A1 | 5/2004 | Azerad et al. |
| 2004/0172044 | A1 | 9/2004 | Grimm et al. |
| 2004/0204760 | A1 | 10/2004 | Fitz et al. |
| 2005/0043835 | A1 | 2/2005 | Christensen |
| 2005/0113846 | A1 | 5/2005 | Carson |
| 2005/0117696 | A1 | 6/2005 | Suzuki et al. |
| 2006/0142657 | A1 | 6/2006 | Quaid et al. |
| 2006/0195111 | A1 | 8/2006 | Couture |
| 2007/0167701 | A1 | 7/2007 | Sherman |
| 2007/0207441 | A1 | 9/2007 | Lauren |
| 2008/0304725 | A1 | 12/2008 | Leitner |
| 2008/0306490 | A1 | 12/2008 | Lakin et al. |
| 2008/0319448 | A1 | 12/2008 | Lavallee et al. |
| 2009/0088674 | A1 | 4/2009 | Caillouette et al. |
| 2009/0092948 | A1 | 4/2009 | Gantes |
| 2009/0099570 | A1 | 4/2009 | Paradis et al. |
| 2009/0220122 | A1 | 9/2009 | Richards et al. |
| 2009/0240141 | A1 | 9/2009 | Neubauer et al. |
| 2009/0281623 | A1 | 11/2009 | Kast et al. |
| 2009/0311647 | A1 | 12/2009 | Fang et al. |
| 2010/0145425 | A1 | 6/2010 | Jung et al. |
| 2010/0145898 | A1 | 6/2010 | Malfliet et al. |
| 2010/0261998 | A1 | 10/2010 | Stiehl |
| 2010/0311028 | A1 | 12/2010 | Bell et al. |
| 2011/0029093 | A1 | 2/2011 | Bojarski et al. |
| 2011/0066072 | A1 | 3/2011 | Kawoos et al. |
| 2011/0087465 | A1 | 4/2011 | Mahfouz |
| 2011/0102549 | A1 | 5/2011 | Takahashi |
| 2011/0117530 | A1 | 5/2011 | Albocher et al. |
| 2011/0196377 | A1 | 8/2011 | Hodorek et al. |
| 2011/0208256 | A1 | 8/2011 | Zuhars |
| 2011/0244415 | A1 | 10/2011 | Batesole |
| 2012/0041318 | A1* | 2/2012 | Taylor ............... A61B 5/02007 600/504 |
| 2012/0063655 | A1 | 3/2012 | Dean et al. |
| 2012/0109228 | A1 | 5/2012 | Boyer et al. |
| 2012/0259592 | A1 | 10/2012 | Liao |
| 2013/0035690 | A1 | 2/2013 | Mittelstadt et al. |
| 2013/0122463 | A1 | 5/2013 | Csillag |
| 2013/0204600 | A1 | 8/2013 | Mehra |
| 2013/0211424 | A1 | 8/2013 | Thiran et al. |
| 2013/0296872 | A1 | 11/2013 | Davison et al. |
| 2013/0297265 | A1 | 11/2013 | Baloch et al. |
| 2013/0310963 | A1 | 11/2013 | Davison |
| 2014/0045167 | A1* | 2/2014 | Anderson ............ G01N 33/483 435/1.2 |
| 2014/0122382 | A1* | 5/2014 | Elster .................... A61B 5/201 706/12 |
| 2014/0329194 | A1 | 11/2014 | Sachdeva et al. |

(56) References Cited

U.S. PATENT DOCUMENTS

| | | |
|---|---|---|
| 2014/0343557 A1 | 11/2014 | Mueller |
| 2015/0272691 A1 | 10/2015 | Kim et al. |
| 2015/0297309 A1 | 10/2015 | Bly et al. |
| 2015/0328004 A1* | 11/2015 | Mafhouz .......... G06F 17/50 700/98 |
| 2016/0038243 A1 | 2/2016 | Miller et al. |
| 2016/0045317 A1 | 2/2016 | Lang et al. |
| 2016/0346091 A1 | 12/2016 | Rahman et al. |
| 2017/0014169 A1 | 1/2017 | Dean et al. |
| 2017/0108930 A1 | 4/2017 | Banerjee et al. |
| 2017/0273797 A1 | 9/2017 | Gordon et al. |

OTHER PUBLICATIONS

Gordon et al.; "Overcoming Cross-Gender Differences and Challenges in Le Fort-Based, Craniomaxillofacial Transplantation With Ehanced Computer-Assisted Technology"; Annals of Plastic Surgery; Oct. 2013, vol. 71, No. 4; pp. 421-428.

Schramm et al.; "Non-invasive Registration in Computer Assisted Craniomaxillofacial Surgery"; Rechner-und Sensorgestutzte Chirurgie, 2001, pp. 258-268.

Bell, R. Bryan; "Computer Planning and Intraoperative Navigation in Orthognathic Surgery"; Journal of Oral and Maxillofacial Surgery; 2011, vol. 69, No. 3, pp. 592-605.

Cevidances, L. et al. Three-dimensional surgical simulation:, American Journal of Orhodontics and Dentofacial Orhopedics, vol. 138, Issue 3, Sep. 2010, pp. 361-371 (Year:2010).

Lee, M. et al., "Custom implant design for patients with craniel defects", Engineering in Medicine and Biology Magazine, IEEE, 2002, vol. 21, pp. 38-44.

Chapuis et al., "A new approach for 3D computer-assisted orthognathic surgery-first clinical case", Elsevier, International Congress Serier, vol. 1281, May 2005, pp. 1217-1222 (Year: 2005).

Chapuis, J. et al., "A New System for Computer-Aided Preoperative Planning and Intraoperative Navigation During Corrective Jaw Surgery", IEEE, Transactions on Information Technology in Biomedicine, vol. 11, No. 3, May 2007, pp. 274-287 (Year: 2007).

Jalbert et al., "One-step primary reconstruction for complex craniofocial re section with PEEK custom-made Implants", Jounal of Cranio-Maxillo-Facial Surgery, Mar. 2014, vol. 42, No. 2, pp. 141-148.

Extended European Search Report dated Jul. 27, 2018 in corresponding EP Application No. 15862375, 8 pages.

Extended European Search Report dated May 24, 2018 in corresponding EP Application No. 15862868, 8 pages.

Murphy et al., "Computer-assisted single-stage cranioplasty", IN: Engineering in Medicine and Biology Sociaty (EMBC), Aug. 25-29, 2015, pp. 4910-4912.

Murphy et al. "Computer-Assisted, Le Fort-Based, Face-Jaw-Teeth Transplantation: A Pilot Study on System Feasibility and Translational Assessment." International journal of computer assisted radiology and surgery, 2014.

Molla: "General Principles of Bone Grafting in Maxillofacial Surgery"; Jan. 2001; The ORION vol. 8; https://pdfs.semanticsholar.org/ec2e/7ba90a835e873687d9454a848842f26c4.pdf.

Goh, R. et al., "Customized fabricated implats after previous failed cranioplasty", Journal of Plastic, Reconstructive and Aesthetic Surgery, Vol. 63, 2010, pp. 1479-1484.

International Search Report and Written Opinion in International Application No. PCT/US2015/062521, 12 pages.

International Search Report and Written Opinion in International Application No. PCT/US2015/062516, 10 pages.

International Search Report and Written Opinion dated Sep. 12, 2016 for PCT/US2016/030447.

International Search Report dated Feb. 24, 2015 from corresponding International Application No. PCT/US2014/067504; 5 pgs.

International Search Report dated Mar. 13, 2015 from corresponding International Application No. PCT/US2014/067167; 5 pgs.

International Search Report dated Mar. 20, 2015 from corresponding International Application No. PCT/US2014/067692; 4 pgs.

International Search Report dated Mar. 5, 2015 from corresponding International Application No. PCT/US2014/067174; 4 pgs.

International Search Report dated Mar. 5, 2015 from corresponding International Application No. PCT/US2014/067656; 5 pgs.

International Search Reported dated Feb. 27, 2015 from corresponding International Application No. PCT/US2014/067581; 4 pgs.

* cited by examiner

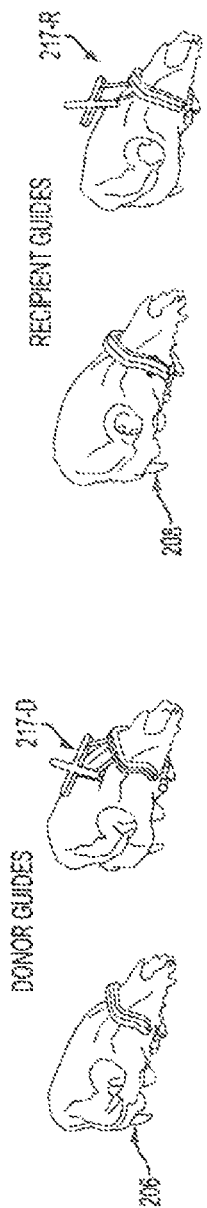
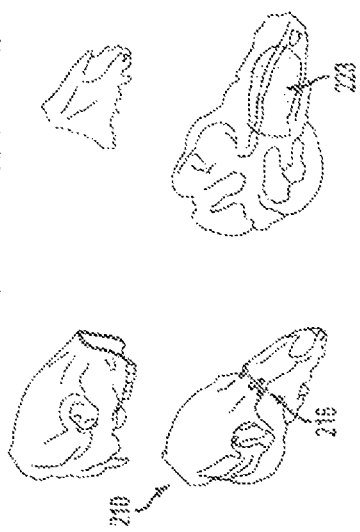
FIG. 8A
FIG. 8B
FIG. 8C

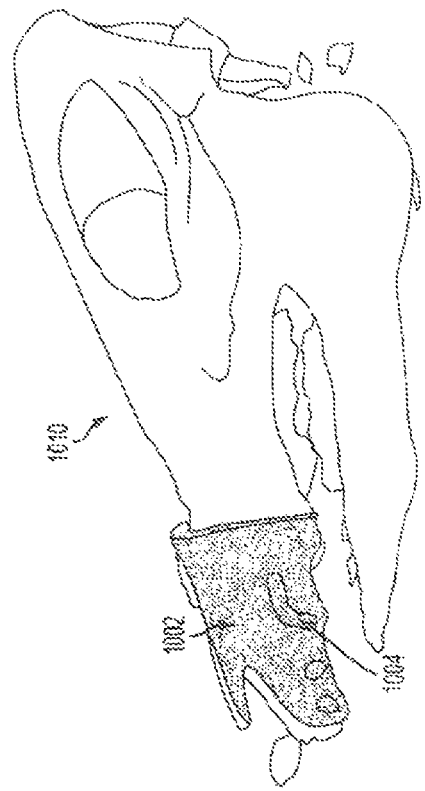
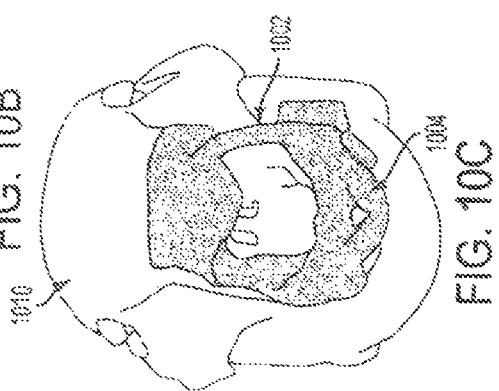
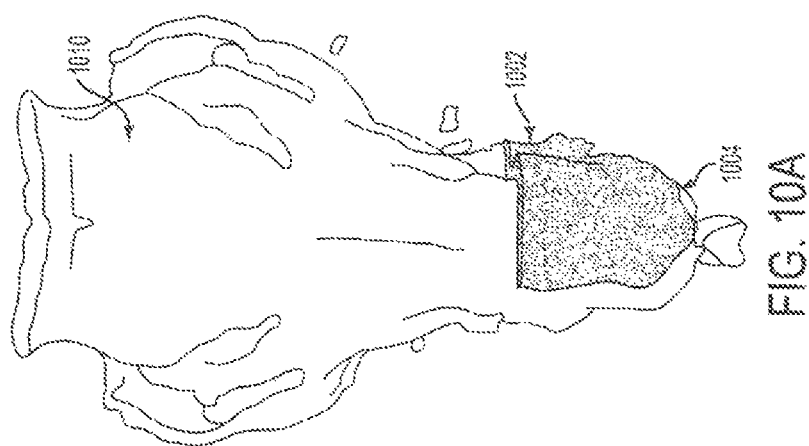

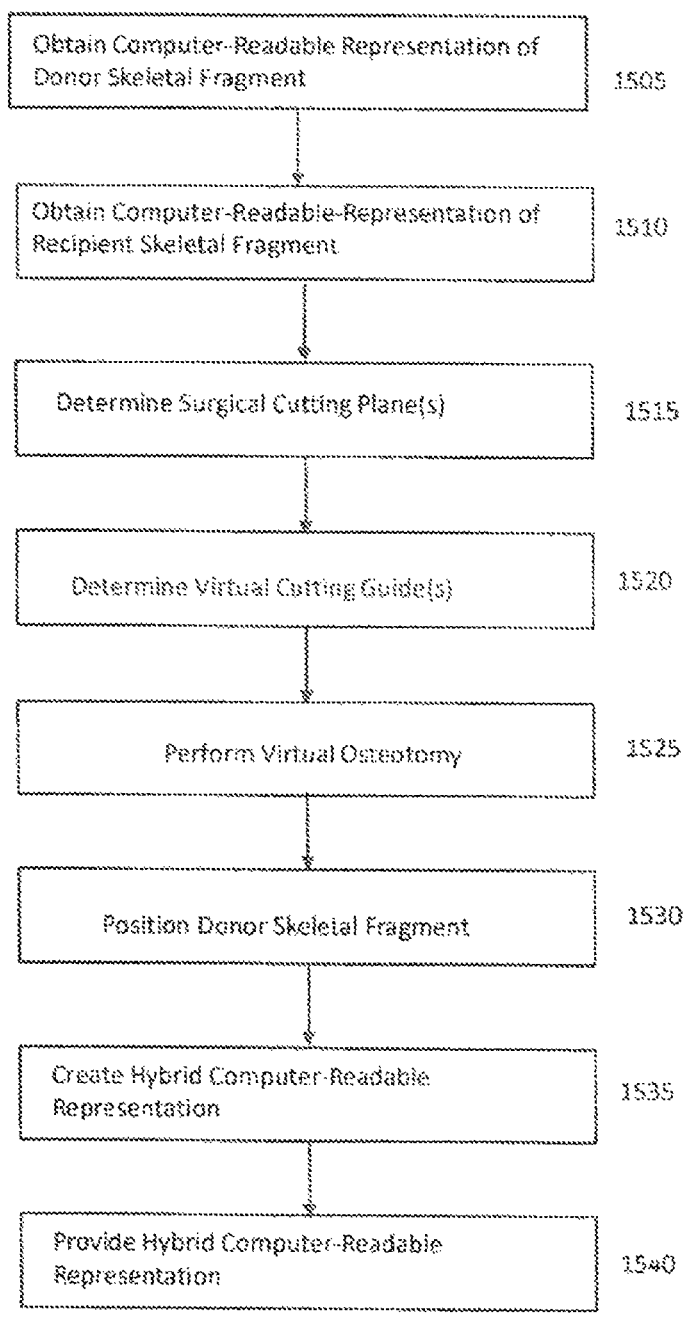

COMPUTER-ASSISTED PLANNING AND EXECUTION SYSTEM

CROSS-REFERENCE TO RELATED APPLICATIONS

This application is a U.S. National Stage application of PCT/US2014/067671 filed 26 Nov. 2014, which claims priority to U.S. Provisional patent application 61/910,204 filed 29 Nov. 2013, U.S. provisional application 61/940,196 filed 14 Feb. 2014, and U.S. provisional application 62/049,866 filed 12 Sep. 2014, the entire disclosures of which are hereby incorporated by reference in their entireties.

GOVERNMENT SUPPORT STATEMENT

This invention was made with government support under Grant Nos. TR000424 and TR001079 awarded by the National Institutes of Health (NIH). The government has certain rights in the invention.

FIELD OF THE INVENTION

This invention relates generally to the field of surgery, particularly craniomaxillofacial surgery, and specifically to the field of computer-assisted craniomaxillofacial surgery and all related orthognathic, neurosurgical and head/face/neck surgical procedures and associated methods, tools and systems.

BACKGROUND OF THE INVENTION

Face-jaw-teeth transplantation represents one of the most complicated scenarios in craniomaxillofacial surgery due to the skeletal, aesthetic, and dental discrepancies between donor and recipient. Use of computer technology to improve accuracy and precision of craniomaxillofacial surgical procedures has been described for nearly 30 years, since the increasing availability of computed topography (CT) prompted the development of a CT-based surgical simulation plan for osteotomies.

Two broad approaches to computer-assisted surgery (CAS), for craniomaxiofacial procedures alike, have gained popularity: 1) pre-operative computer surgical planning which may or may not include the use of three-dimensional computer manufactured surgical guides (3D CAD/CAM) to cut and reposition bone and soft tissue, and 2) utilizing intraoperative, image-based feedback relative to preoperative imaging for the surgeon to provide more objective data on what is happening beyond the "eyeball test". However, none are meant for real-time guide placement feedback in areas where accurate guide placement may become challenging, such as the three-dimensional facial skeleton. Also, there are no single platforms built to provide BOTH planning AND navigation—with seemless integration Additionally, standard off-the-shelf vendor computer-assisted surgery systems may not provide custom features to mitigate problems associated with the increased complexity of this particular procedure. Furthermore, there are currently no validated methods for optimizing outcomes related to facial (soft tissue), skeletal (hard tissue), and occlusal (dental) inconsistencies in the setting of donor-to-recipient anthropometric mismatch in real-time—a major hurdle to achieving this specialty's full potential.

One known system includes pre-operative planning and fabrication of cutting guides by way of computer manufactured stereolithographic models for human facial transplantation. However, such a system uses standard off-the-shelf vendor systems and does not include necessary features to mitigate the increased complexity of this particular procedure in regards to accurate guide placement and optimizing outcomes.

Additionally, known CAS paradigms for craniomaxillofacial surgery provide little capacity for intraoperative plan updates. This feature becomes especially important since in some circumstances during the transplantation surgery, it may be necessary to revise and update the preoperative plans intraoperatively.

What is needed in the art, therefore, is a single, fully-integrated platform, providing a computer-assisted surgery solution customized for pre-operative planning, intraoperative navigation, and dynamic, instantaneous feedback for—in the form of biomechanical simulation and real-time cephalometrics—guide placement and outcome optimization of facial transplantation. Such system has the potential to improve outcomes across both the pediatric and adult-based patient population.

SUMMARY

In an embodiment, there is a method for performing a medical procedure. The method can include creating a first 3D reconstruction of a skeleton, selecting a cut plane to bisect the 3D reconstruction, and forming a reference guide. The reference guide can include an attachment surface configured for attaching to a skeletal feature, and a navigation surface connected to the attachment surface and comprising a trackable reference geometry. The attachment surface can include a contoured surface corresponding to a geometry defined by the interface of the cut-plane and contours of portions of the skeletal feature. The attachment surface can be configured for attaching to the skeleton at a location substantially corresponding to a preselected location.

In another embodiment there is a medical procedure, comprising: attaching a first cranial reference unit to a skeleton; attaching a first fragment reference unit to a skeleton fragment; tracking locations of the first cranial reference unit and the first fragment reference unit with a first tracker, creating a first 3D reconstruction of the skeleton with a first virtual cranial reference unit and first virtual fragment reference unit superimposed on the first 3D reconstruction at locations that corresponds to relative positions of the first cranial reference unit and the first fragment reference unit; superimposing a first virtual reference guide on the first 3D reconstruction at a location that corresponds to a proposed placement of an actual reference guide relative to the location of the first cranial reference unit or the location of the first fragment reference unit; forming a first virtual fragment by segmenting the 3D reconstruction of the skeleton at a location adjacent to the first virtual reference guide; superimposing the first virtual fragment on the 3D reconstruction of the skeleton to form a hybrid 3D reconstruction, and performing an automated cephalometric computation for the hybrid reconstruction.

In another embodiment, there is a computing system for managing medical procedures. The system can comprise: at least one memory to store data and instructions; and at least one processor configured to access the at least one memory and to execute instructions. The instructions can comprise: track the locations of a first fragment reference unit with respect to first cranial reference unit, generating a first 3D reconstruction of the skeleton with a first virtual cranial reference unit and first virtual fragment reference unit superimposed on the first 3D reconstruction at locations that corresponds to relative positions of the first cranial reference unit and the first fragment reference unit; superimposing a planned reference plane over portions of the first 3D reconstruction; generating a first virtual reference guide having a geometry that corresponds to an interface between intersecting portions of the planned reference plane and the first 3D reconstruction; controlling a device for manufacturing a reference guide according to the geometry of the first virtual reference guide; forming a first virtual fragment by segmenting the 3D reconstruction of the donor skeleton at a location adjacent to the first virtual reference guide; generating a second 3D reconstruction of the skeleton with the virtual reference guide superimposed on the first 3D reconstruction at a location that corresponds to a relative position of a reference guide; performing a cephalometric analysis of the first 3D reconstruction and the second 3D reconstruction; and superimposing the first virtual fragment on the second 3D reconstruction of the skeleton.

Advantages of at least one embodiment include 1) intraoperative plan updates based on hard tissue discrepancies between planned and executed procedure; 2) on-table feedback in the form of dynamic, real-time cephalometrics; and 3) pre-designed fixation plates matching the virtual plan.

Another advantage of at least one embodiment includes increasing the robustness of conventional CAS paradigms by providing a robust surgical system to deal with situations in which tools and templates designed and fabricated preoperatively may not entirely address intraoperative surgical needs. Robustness of the planning and navigation strategy is especially important in total face transplantation given the long operating times.

Another advantage of at least one embodiment includes improved outcomes and decreased accompanying morbidity via shortened operative times, more precise surgical maneuvers, and improved margin of safety.

A computer-implemented method for computer-assisted planning of a transplant surgery is disclosed. The method can comprise obtaining a computer-readable representation of a donor skeletal fragment, obtaining a computer-readable representation of a recipient skeletal fragment; determining one or more surgical cutting planes on the computer-readable representation of the donor skeletal fragment from which a portion of the donor skeletal fragment will be harvested from the computer-readable representation of the donor skeletal fragment; determining one or more virtual cutting guides based on the one or more surgical cutting planes to be attached to the computer-readable representation of the donor skeletal; performing a virtual osteotomy to separate the portion of the donor skeletal fragment from the computer-readable representation of the donor skeletal fragment from a remainder portion of the donor skeletal fragment based on a position of the one or more virtual cutting guides that are attached to the computer-readable representation of the donor skeletal fragment; positioning the donor skeletal fragment within a transplant region of the recipient skeletal fragment; creating a hybrid computer-readable representation comprising the recipient skeletal fragment and the portion of the donor skeletal fragment during or after the positioning; and providing the hybrid computer-readable representation as an output.

The computer-implemented method can further comprise creating the computer-readable representation of a recipient skeletal fragment based on one or more medical imaging techniques, wherein the computer-readable representation of the recipient skeletal fragment comprises one or more of: a vascular model or a neural model of the recipient skeletal fragment; and creating the computer-readable representation of a donor skeletal fragment based on one or more medical imaging techniques, wherein the computer-readable representation of the donor skeletal fragment comprises one or more of: a vascular model or a neural model of the donor skeletal fragment.

The computer-readable representation of the recipient skeletal fragment and the donor skeletal fragment can comprise a segmented 3D reconstruction model that is created using the one or more medical imaging techniques and a segmentation algorithm, wherein each voxel of the segmented 3D reconstruction model of the recipient skeletal fragment and the donor skeletal fragment comprises an associated anatomical attribute that classifies an anatomy for which each voxel represents.

The computer-implemented method can further comprise tracking movement of the donor skeletal fragment of the computer-readable representation during the positioning; updating the hybrid computer-readable representation based on the movement being tracked.

The computer-implemented method can further comprise identifying a set of cephalometric landmarks associated with the hybrid computer-readable representation; calculating a set of cephalometric metrics for the set of cephalometric landmarks that are identified; and determining an acceptable result of the surgery being planned based at least in part on the set of cephalometric metrics that are calculated.

The set of cephalometric landmarks can comprise one or more of: Gonion ("Go"), Nasion ("N"). A point ("A"), B point ("B"), Sella ("S"), Menton ("M"), left/right Zygoma ("ZY"), Os occipital ("OCC").

The computer-implemented method can further comprise updating at least one of the one or more surgical cutting planes or cutting guides based on the determination of acceptable result.

The computer-implemented method can further comprise comparing the set of cephalometric metrics that were calculated based on a set of baseline cephalometric metrics.

A system for computer-assisted planning of a transplant surgery is disclosed. The system can comprise at least one memory storing instructions; and at least one processor coupled to the memory and executing the instructions to perform a method of computer-assisted planning of a transplant surgery. The method can comprise obtaining a computer-readable representation of a donor skeletal fragment; obtaining a computer-readable representation of a recipient skeletal fragment; determining one or more surgical cutting planes on the computer-readable representation of the donor skeletal fragment from which a portion of the donor skeletal fragment from the computer-readable representation of the donor skeletal fragment will be harvested; determining one or more virtual cutting guides based on the one or more surgical cutting planes to be attached to the computer-readable representation of the donor skeletal fragment; performing a virtual osteotomy to separate the portion of the donor skeletal fragment from the computer-readable representation of the donor skeletal fragment from a remainder portion of the donor skeletal fragment based on a position of the one or more virtual cutting guides that are attached to the computer-readable representation of the donor skeletal fragment; positioning the donor skeletal fragment within a transplant region of the recipient skeletal fragment; creating a hybrid computer-readable representation comprising the recipient skeletal fragment and the portion of the donor skeletal fragment during or after the positioning; and providing the hybrid computer-readable representation as an output.

A non-transitory computer-readable medium including instructions to perform a method for computer-assisted planning of a transplant surgery is disclosed. The method can comprise obtaining a computer-readable representation of a donor skeletal fragment; obtaining a computer-readable representation of a recipient skeletal fragment; determining one or more surgical cutting planes on the computer-readable representation of the donor skeletal fragment from which a portion of the donor skeletal fragment from the computer-readable representation of the donor skeletal fragment will be harvested; determining one or more virtual cutting guides based on the one or more surgical cutting planes to be attached to the computer-readable representation of the donor skeletal fragment; performing a virtual osteotomy to separate the portion of the donor skeletal fragment from the computer-readable representation of the donor skeletal fragment from a remainder portion of the donor skeletal fragment based on a position of the one or more virtual cutting guides that are attached to the computer-readable representation of the donor skeletal fragment; positioning the donor skeletal fragment within a transplant region of the recipient skeletal fragment; creating a hybrid computer-readable representation comprising the recipient skeletal fragment and the portion of the donor skeletal fragment during or after the positioning; and providing the hybrid computer-readable representation as an output.

Additional advantages of the embodiments will be set forth in part in the description which follows, and in part will be understood from the description, or may be learned by practice of the invention. The advantages will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

BRIEF DESCRIPTION OF THE DRAWINGS

FIG. 5A shows donor's face-jaw-teeth alloflap in suboptimal position as compared to recipient's cranium FIG. 5B shows appropriate face-jaw-teeth positioning with immediate surgeon feedback and updated cephalometric data pertinent to a pre-clinical investigation. A surgeon may adjust the position of face-jaw-teeth segment upwards, downwards, forwards or backwards based on this real-time cephalometric feedback—since this information helps to predict optimal form and function. For instance, placing the face-jaw-teeth segment forward may improve the patient's airway, but if moved too far forward, it may cause at the same time the patient to have a significant overjet (i.e. malocclusion) and abnormal appearance on profile view.

FIG. 8A illustrates a donor face-jaw-teeth alloflap recovery, FIG. 8C shows recipient preparation prior to transplant, FIG. 8C illustrates custom pre-bent fixation plate and palatal splint designed to achieve face-jaw-teeth alignment and skeletal inset with standard technique.

FIGS. 10A-10C are top-view (bird's eye view), left-sided profile view, and frontal view, respectively, of images displayed by an imaging system of a surgical system of the embodiments. The images depict a recipient skeleton and include real-time assessment of planned versus actual face-jaw-teeth positions.

FIG. 15 illustrates an example method of a computer-implemented method for computer-assisted planning of a transplant surgery, according to the present teachings.

DESCRIPTION OF THE EMBODIMENTS

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

The following embodiments are described for illustrative purposes only with reference to the Figures. Those of skill in the art will appreciate that the following description is exemplary in nature, and that various modifications to the parameters set forth herein could be made without departing from the scope of the present invention. It is intended that the specification and examples be considered as examples only. The various embodiments are not necessarily mutually exclusive, as some embodiments can be combined with one or more other embodiments to form new embodiments.

Disclosed are embodiments of a computer-assisted surgery system that provides for large animal and human pre-operative planning, intraoperative navigation which includes trackable surgical cutting guides, and dynamic, real-time instantaneous feedback of cephalometric measurements/angles as needed for medical procedures, such as facial transplantation, and many other instances of craniomaxillofacial and orthognathic surgery. Such a system can be referred to as a computer-assisted planning and execution (C.A.P.E.) system and can be exploited in complex craniomaxillofacial surgery like Le Fort-based, face-jaw-teeth transplantation, for example, and any type of orthognathic surgical procedure affecting one's dental alignment, and can include cross-gender facial transplantation.

Figure 1:
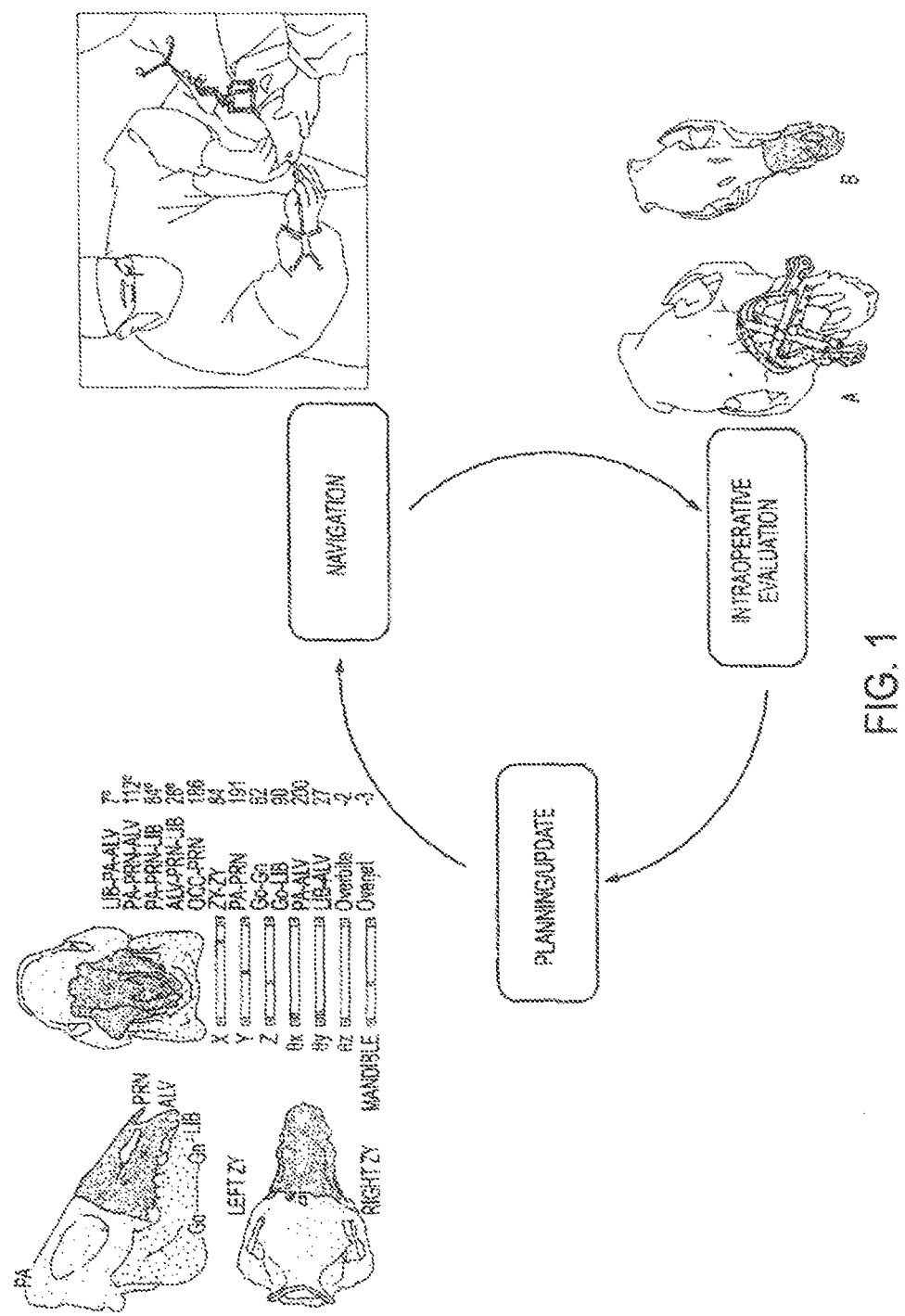
FIG. 1 is a flowchart of general features of a surgical system of an embodiment closes the loop between surgical planning, navigation and enabling intraoperative updates to the plan.
Figure 2A:
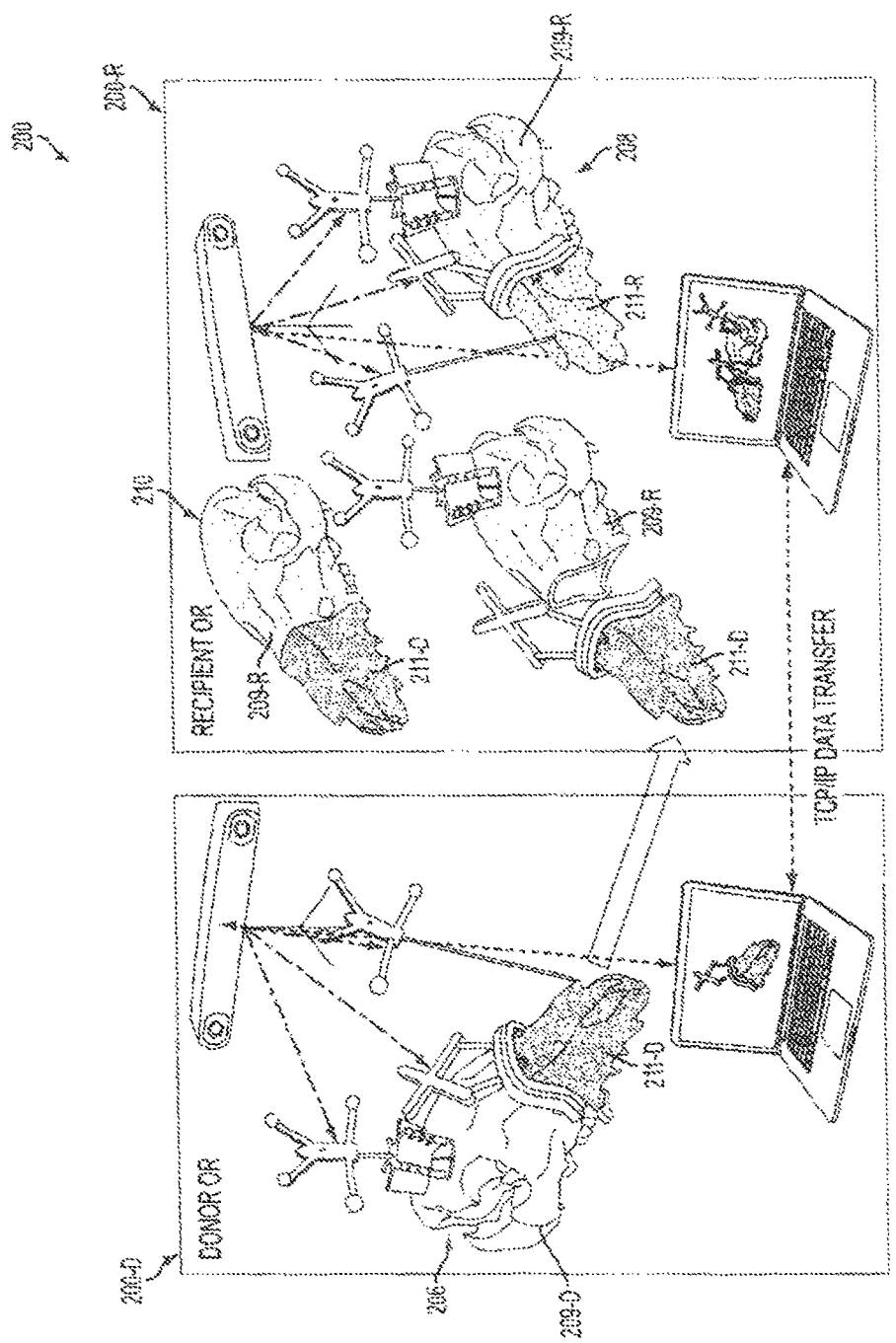
FIGS. 2A-2C provide a schematic overview of a surgical system of an embodiment.
Figure 2B:
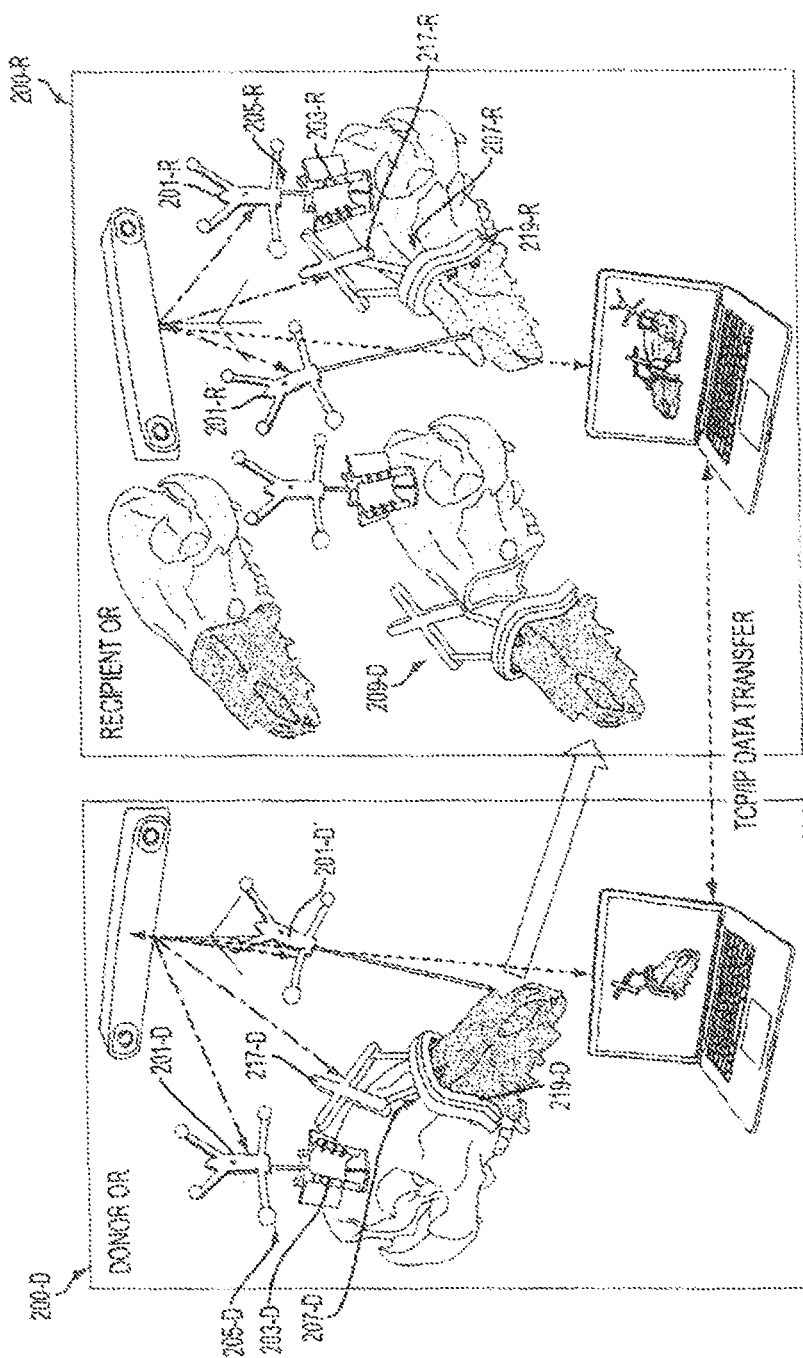
Figures 2C, 2D, 2E, 2F, 2G:
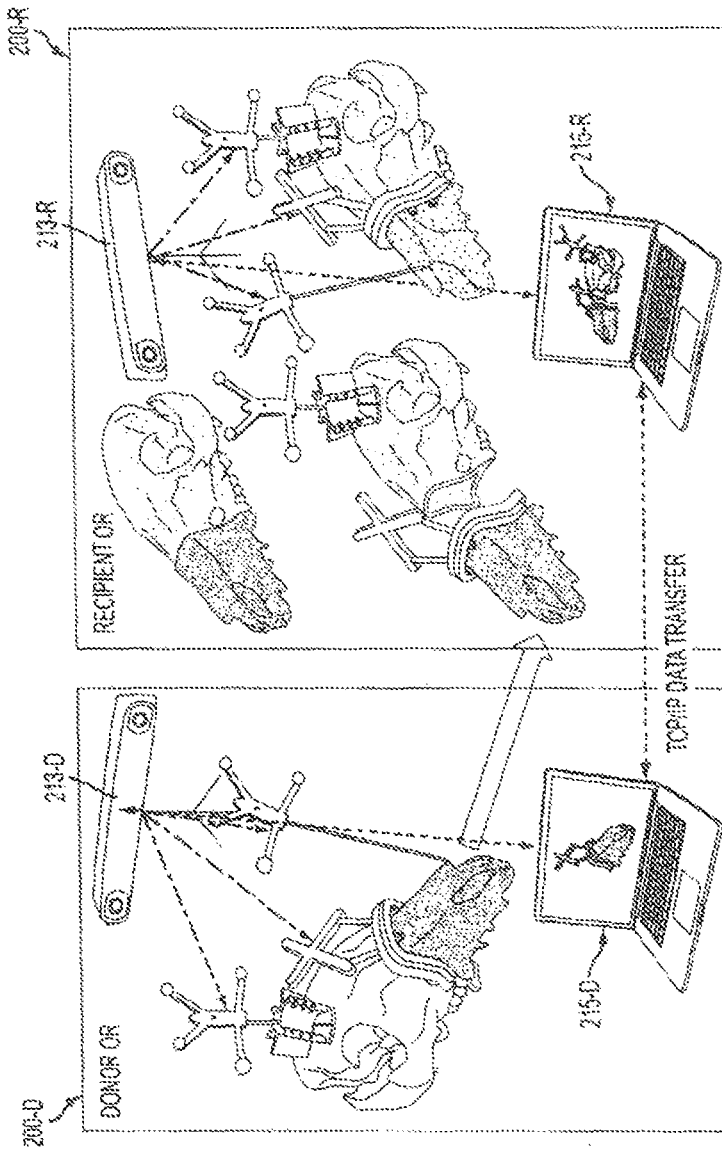
FIGS. 2D-2G are graphical representations of some components and/or features of the surgical system of FIGS. 2A-2C.

The fundamental paradigm for CAS involves developing a surgical plan, registering the plan and instruments with respect to the patient, and carrying out the procedure according to the plan. Embodiments described herein include features for workstation modules within a CAS paradigm. As shown in FIG. 1, a surgical system of the embodiments can enable intraoperative evaluation of a surgical plan and can provide instrumentation for intraoperative plan updates/revisions when needed.

Embodiments can include a system with integrated planning and navigation modules, for example, a system for tracking donor and recipient surgical procedures simultaneously. In general, features of such a system can include: 1) two networked workstations concurrently used in planning and navigation of the two simultaneous surgeries for both donor and recipient irrespective of geographic proximity. 2) two trackers, such as electromagnetic trackers, optical trackers (e.g., Polaris, NDI Inc.), and the like, for tracking bone fragments, tools, and soft tissues, 3) novel guides, reference kinematic markers, etc. as required for navigation. These feature re described in further detail with respect to FIGS. 2A-2G.

Preoperative planning can include the following tasks: a) segmentation and volumetric reconstruction of the donor and recipient facial anatomy, b) planning for patient-specific cutting guide placement; c) cephalometric analysis and biomechanical simulation of the hybrid skeleton's occlusion and masticatory function, respectively; d) Fabrication of the hybrid cutting guides enabling both geometric ("snap-on" fit) and optical navigation; e) 3D mapping the vascular system on both recipient and donor facial anatomy; f) plan updates, if necessary, based on the feedback from the intraoperative module. As used herein, "snap-on fit" or "snap-on" or "snap on" is used to describe the way an item, such as a cutting guide, attaches to a predetermined area. That is, the cutting guide actually "snaps-on" to a certain pre-determined area along the facial skeleton, and in all other areas it doesn't fit properly since size and width varies throughout significantly with many convexities and concavities.

Intraoperative tasks of embodiments described herein can generally include: 1) registration of the preoperative model reconstructed from the CT data to donor and recipient anatomy; 2) visualization (using information from the tracker, such as an electromagnetic tracker, optical tracker, and the like) of the instruments and cutting guides to help the surgeon navigate; 3) verify the placement of cutting guides, and performing real-time cephalometric and biomechanical simulation for occlusion analysis, if, for any reason, the osteotomy sites need to be revised; 4) dynamically tracking the attachment of the donor fragment to the recipient and provide quantitative and qualitative (visual) feedback to the surgeon for the purpose of improving final outcomes related to form (i.e. overall facial aesthetics) and function (i.e. mastication, occlusion relation, airway patency). Such a procedure is described in further detail below with respect to FIG. 3.

Preparative Planning

In general, a method for performing a surgery includes a virtual surgical planning step that includes performing segmentation and 3D reconstruction of recipient and donor CT scans (e.g., Mimics 15.01, Materialise, Leuven Belgium). Virtual osteotomies can then be performed within the software to optimize the donor/recipient match. Patient-customized cutting guide templates can then be created (3-matic 7.01, Materialize, Leuven, Belgium). These templates can then be rapid prototyped via an additive manufacturing modeling process, which can include, but is not limited to, stereolithography or 3D printing and the like. The surgical method and system for performing surgery are described in further detail below.

Figure 4B:
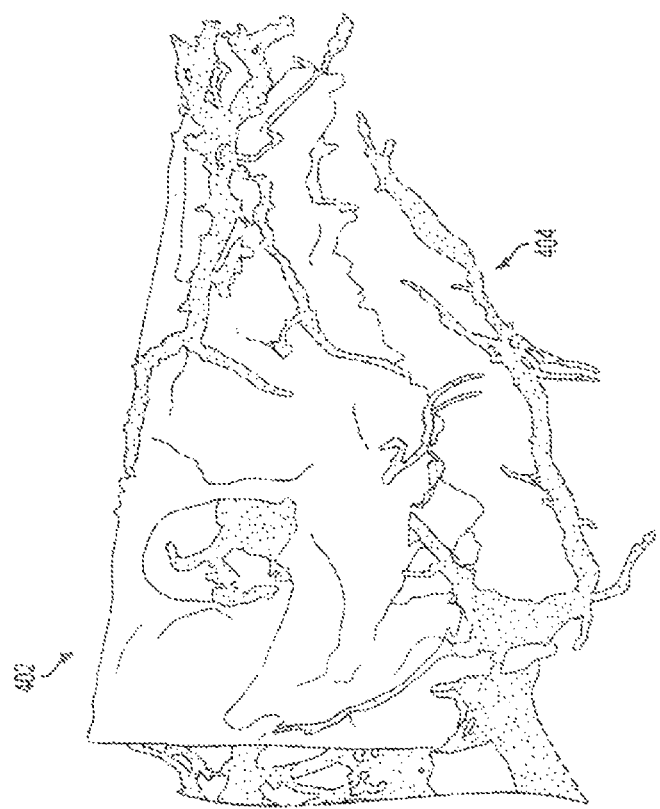
FIG. 4B shows a Segmented arterial system of craniomaxillofacial skeleton generated from CT angiography (CTA) data allowing 3D, intraoperative mapping.
Figure 4A:
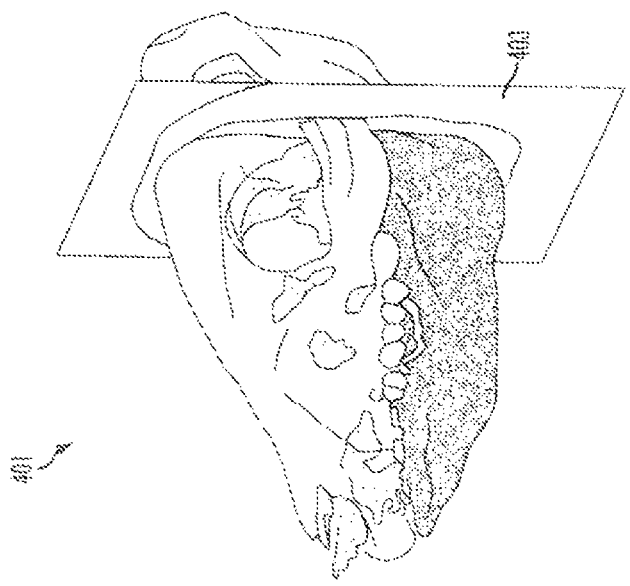
FIG. 4A is a CT-scan of reconstructed images of size-mismatched facial skeleton generated from segmentation software utilized for preoperative planning.
Figure 5A:
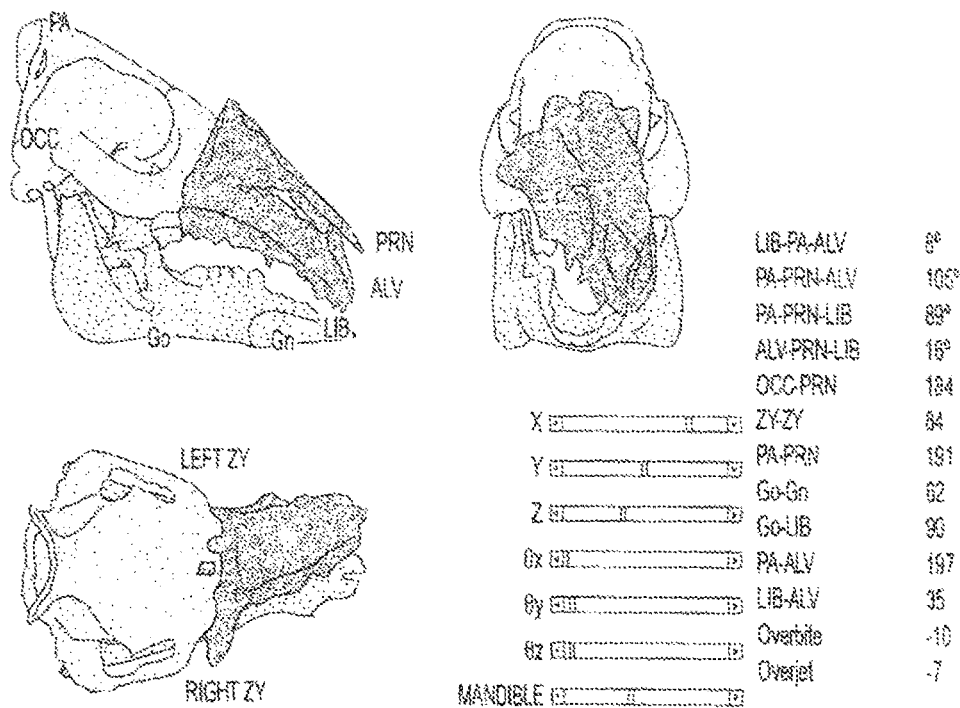
FIGS. 5A-5B shows depictions of on-screen images provided by a surgical system, such as the surgical system of FIG. 2A displaying real-time, dynamic cephalometrics and pertinent measurements applicable to humans.
Figure 5B:
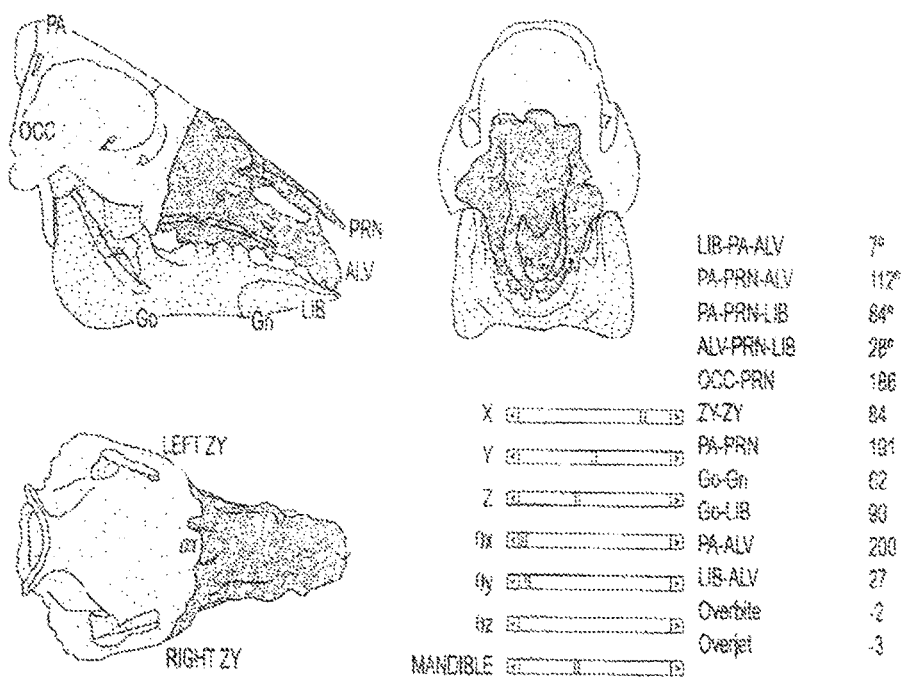

Referring to FIGS. 4A and 4B, during the initial planning stage, surgeons determine a virtual plan 401 based on the recipient's craniomaxillofacial deformity irrespective of the donor. From registered CT data, segmentation software generates volume data for specific key elements (e.g., the mandible, maxilla, and cranium) used for preoperative planning and visualization. The planning workstation automatically generates the expected cut geometry of the donor fragment 402 together with the recipient, thereby defining the predicted facial skeleton with accompanying hybrid occlusion. If available, blood vessels 404 are segmented from CT angiography scans as shown in FIG. 4B. That is, in an embodiment nerves (via known nerve foramens) and vessels (both arteries and veins) can be localized to provide a full anatomical "road map" to the surgeons for a more precise, time-saving anatomical dissection with perhaps decreased blood loss and smaller incisions. The planning module can also perform static cephalometric analysis and evaluation of face-jaw-teeth harmony via biomechanical simulation on varying constructions of the hybrid donor and recipient jaw, such as that shown in FIGS. 5A-5B. Using this tool, the surgeon can evaluate different placements for the donor's face-jaw-teeth alloflap on the recipient's facial skeleton in relation to orbital volumes, airway patency, facial projection, and dental alignment. An automated cephalometric computation for the hybrid face indicates the validity of the planned surgery from both an aesthetic, functional and reconstructive standpoint based on various measurements of pertinent landmarks as shown, for example, in Tables 1A-B.

TABLE 1A

Pertinent landmarks for cephalometric analysis.
Note that any other cephalometric landmark and/or angle
can also be used with this CAPE system.

| SYMBOL | NAME and DEFINITION |
|---|---|
| Go | Gonion: a point mid-way between points defining angles of the mandible |
| Gn | Gnathion: most convex point located at the symphysis of the mandible |
| ALV | Alveolare: mid-line of alveolar process of the upper jaw, at incisor - alveolar junction |
| LIB | Lower Incisor Base: midline of anterior border of alveolar process of mandible at the incisor- alveolar junction |
| PA | Parietale: most superior aspect of skull in the midline, (formed by nuchal crest of occipital bone and parietal bone) |
| PRN | Pronasale: bony landmark representing anterior limit of nasal bone |
| ZY | Zygion: most lateral point of malar bone |
| OCC | Occipital region: midpoint between the occipital condyles | as a polymer, and can include an attachment surface 216 configured for attaching to a skeletal feature, and can have a "snap-on" fit to both donor and recipient. As described above, the attachment surface comprises a contoured surface that corresponds to contours of the skeletal feature within the planned cut planes. A navigation surface, such as a reference geometry 217 connected, built into, or attached to the guide structure directly or via attachment guides (not shown) enables dynamic intraoperative tracking of guides with respect to the patient's skeleton. Palatal splints ensure planned dento-skeletal alignment fixation following Le Fort-type facial transplants or any similar type of surgery. Fixation plates 216 can include a primary surface 216' and a plurality of fixation surfaces 221, such as eyelets, for screw placement to provide rigid immobilization at the irregular skeletal contour areas along various donor-to-recipient interfaces. Having pre-bent fixation plates decreases total operative times and helps to confirm accurate skeletal alignment by overcoming step-off deformities at bone-to-bone interfaces. Accordingly, at least one of the plurality of fixation surfaces can be located on one side of the primary surface and configured for attaching the fixation surface to a donor skeleton fragment, and at least one of another of the plurality of fixation surfaces is located on another side of the primary surface and configured for attaching the fixation surface to a recipient skeleton. The whole fixation plate or just portions of the fixation plate, such as the primary surface or fixation surfaces can be manufactured via additive manufacturing technology.

The cutting guide's navigation surface can include trackable objects, for example, on the reference geometry, such as infrared (IR) reflective coatings or IR emitters. For example,

TABLE 1B

Cephalometric measurements and related units.

| Measure | ZY-ZY | PA-PRN | Go-Gn | Go-LIB | PA-ALV | LIB-ALV | Overbite | Overjet | OCC-PRN | LIB-PA-ALV | PA-PRN-ALV | PA-PRN-LIB | ALV-PRN-LIB |
|---|---|---|---|---|---|---|---|---|---|---|---|---|---|
| Units | mm | mm | mm | Mm | mm | mm | mm | mm | mm | deg | deg | deg | deg |

To evaluate and predict cephalometric relationships both during planning and intra-operative environments, the system can use validated, translational landmarks between swine and human to thereby allow effective pre-clinical investigation. The cephalometric parameters defined by these landmarks can be automatically recalculated as the surgeon relocates the bone fragments using a workstation's graphical user interface.

Figure 6:
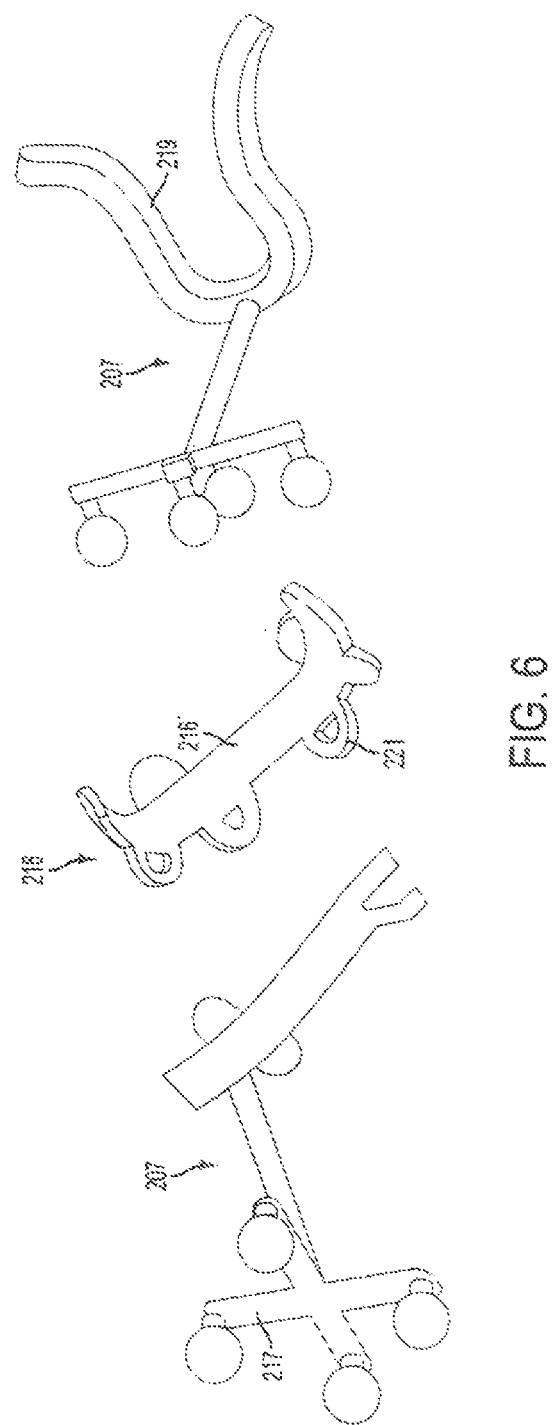
FIG. 6 shows some pre-bent fixation plates with screw holes designed virtually to accommodate the donor-to-recipient skeletal mismatch areas and matching navigational cutting guides of a surgical system, for example, the surgical system of FIGS. 2A-2C.

Preoperative planning can also involve fabrication of custom guides 207 as shown in FIG. 6 and palatal splints 223 as illustrated in FIG. 8C. Planned cut planes 403 (as shown in FIG. 4) can be used for defining the geometry of the cutting guides to thereby provide patient-specific cutting guides. These cutting guides can be designed according to the skeletal features through which the cutting plane intersects, such as an outer skeletal surface of a cross section defined by the cutting plane, and can be fabricated via stereolithography, or via any additive manufacture technology. In an embodiment, custom cutting guide templates can be separately designed and navigational registration elements can be added (Freeform Plus, 3D Systems, Rock Hill, S.C.). As discussed above, the surgical guides can be manufactured via additive manufacturing technology (AMT). The cutting guides can, therefore, be a 3D printing material such the trackable objects can include a plurality of integrated tracking spheres, each of which has an IR reflection surfaces.

Intraoperative Surgical Assistance

Figure 7A:
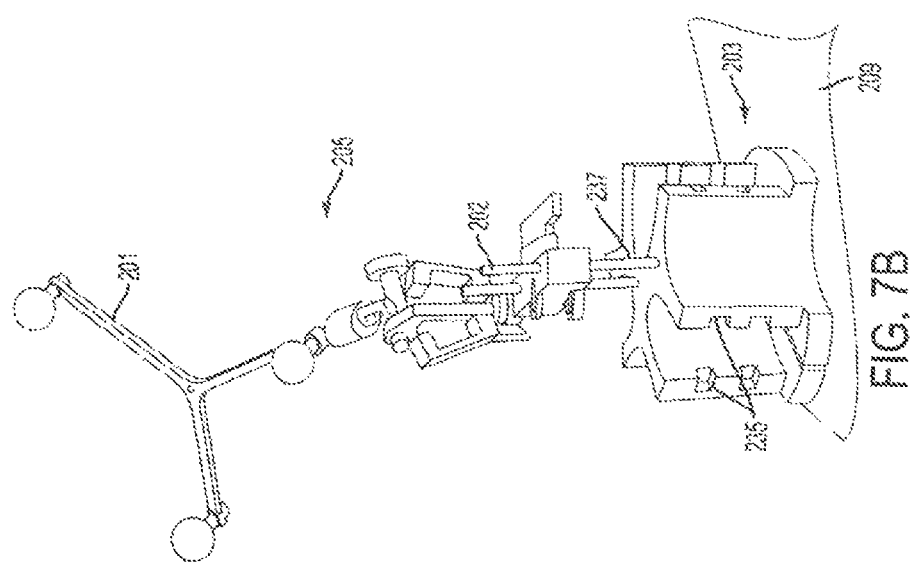
FIG. 7A is a photograph of a kinematic reference mount of an embodiment as it is affixed onto a donor's cranium with intermaxillary screws. A permanent suture (not visible) attaches stabilizers, such as springs and/or cross bars, which allow easy removal and replacement during surgery.
Figure 7B:
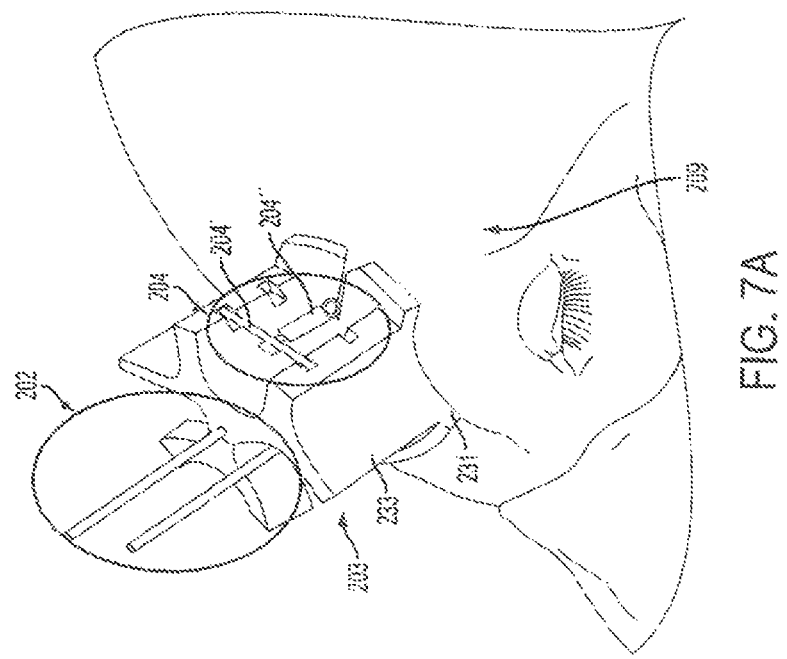
FIG. 7B is a photograph of a detachable rigid body with reflective markers attached to the reference body FIGS. 8A-8C include illustrations of cutting guides of the embodiments with navigational capabilities.

Individual navigation for both donor and recipient surgeries tracks the cutting guides with respect to planned positions. Surgeons can attach a reference unit, such as a kinematic reference mount to three intramedullary fixation (IMF) screws arranged in a triangular pattern on each the donor and recipient craniums as shown in FIG. 7A-7B. Accordingly, in an embodiment, there is a reference unit 205 for providing real-time surgical navigation assistance. The reference unit for providing real-time surgical navigation assistance can include a kinematic mount 203, at least one fixation rod 202, at least one support 204, and reference geometry 201. The kinematic mount 203 can include a base with a plurality of recesses defined by sidewalls 233, at least one pair of slots 235 defined by portions of the sidewalls, with each slot of the pair formed across the recess from the other slot, and at least one guide hole 237 extending through a length of the fixation plate. The at least one fixation rod 202 can extend through the at least one guide hole 237. An end of the at least one support rod can be configured for attaching to a skeleton of a being 209. The at least one support can be disposed in the pair of slots and can be configured to attach to the being. The reference geometry 201 can be attached to the at least one fixation rod.

The at least one support 204 can include at least one cross-bar 204' with ends that are configured for placement in the slots 235, and a spring 204" attached at one end to the at least one cross-bar 204' and attached at another end to the patient (e.g., a human-being). The spring attached at another end to the being can be attached via a suture (further described below). The 205 can further include a trackable object disposed on the reference geometry. The trackable object disposed on the reference geometry can include an IR reflective surface. The mount 203 can be made via additive manufacturing techniques and can therefore comprise a polymer. The at least one fixation rod can include a plurality of intramedullary fixation screws. The base can be configured for being detachably mounted on the skeleton of the being. The intramedullary fixation screws can be arranged in a triangular pattern. Accordingly the guide-holes can be configured in a triangular pattern on the base.

Accordingly, the mount design permits flexibility in the placement of the IMF screws so that no template is necessary. A spring 204" can attach to each IMF screw via suture threaded through, for example, the eyelets. These springs hold the cranial mount 203 in place and allow easy removal and replacement of the cranial mount (e.g. during positional changes required for bone cuts and soft tissue dissections). The key design advantages of the reference are detachability and use of Intramaxillary fixation (IMF) screws for stable attachment.

The reference geometry 201 (e.g., which can be purchased from Brainlab, Westchester, Ill., USA) attached to the kinematic mount 203 provides a static coordinate frame attached to the patient. The surgeon can digitize three bony landmarks (e.g. the inferior aspect of the orbits and antero-superior maxilla) to define a rough registration between the environment and virtual models. For example, three, consistent points can be selected which can be quick to find, easy to reproduce on numerous occasions, and would remain constant irrespective of the user and his/her experience with the systems of the embodiments. The surgeon can thereby collect several point sets from exposed bone using a digitization tool and uses an iterative closest point registration technique to refine the registration. As shown in FIG. 8, once registered, the surgeon navigates the placement of the cutting guide 217 using the combination of "snap-on" geometric design and the tracking system coupled to visual feedback. This allows assessment of inaccuracies related to soft tissue interference, iatrogenic malpositioning, anatomical changes since acquiring original CT scan data, and/or imperfections in cutting guide design or additive manufacturing process.

Self-drilling screws affix the cutting guide to the patient's skeleton to ensure osteotomies are performed along predefined planes, maximizing bony congruity. After dissecting the donor's maxillofacial fragment and preparing the recipient's anatomy, the surgical team transfers the facial alloflap. The system is configured to track the final three-dimensional placement of; for example, the Le Fort-based alloflap providing real-time visualization such as that shown in FIG. 5A-5B. This provides real-time visualization of important structures such as new-orbital volumes (vertical limit of inset), airway patency (posterior horizontal limit of inset), and facial projection (anterior horizontal limit of inset). Once confirmed, the surgeon fixates the donor alloflap to the recipient following conventional techniques with plates and screws.

Accordingly, returning to FIG. 2A-2G, there is a system 2000 for tracking donor and recipient surgical procedures simultaneously. The system can include a donor sub-system 200-D, a recipient sub-system 200-R and a communications link (indicated by the horizontal dotted-line) such as a communication link that provides TCP/IP data transfer between the donor and recipient sub-systems. The donor sub-system can include a first computer workstation 21S-D, a first cranial reference module 205-D, a first cutting guide 207-D for attaching to a preselected location of a donor skeleton 206, a first fragment reference module 201-D', and a first tracker 213-D. The first cutting guide 207-D can include an attachment surface 219-R configured for attaching to a skeletal feature, and a navigation surface 217-D connected to the attachment surface and comprising a trackable reference geometry. The first tracker 213-D may be configured to be in communication with the first computer workstation, for example, via a communications link. The first tracker can be configured to track, for example via IR optical tracking, a location of a portion of the first cranial reference module, a portion of the first cutting guide and a portion of the first fragment reference module. The recipient sub-system 200-R can include a second computer workstation 215-R, a second cranial reference module 205-R, and a second tracker 213-R. The second tracker 213-R can be configured to be in communication with the second computer workstation, for example, via a communications link. The second tracker can be configured to track, for example, via IR optical tracking, a location of a portion of the second cranial reference module. The communications link can connect the first computer workstation and the second computer workstation such that the first computer workstation and second computer workstation are able to communicate.

The recipient sub-system 200-R can further include a second fragment reference unit 201-R. The second tracker 213-R can further be configured to track a location of a portion of the second fragment unit.

The recipient sub-system 200-R can further include a second cutting guide 219-R for attaching to a preselected location of a recipient skeleton 208. The second tracker 213-R can further be configured to track a location of a portion of the second cutting guide.

Additionally, when a surgeon has removed the donor skeletal fragment from the donor, it can then be transferred for attachment onto the recipient. Accordingly, the second tracker 213-R can be further configured to track a location of a portion of the first cutting guide 207-D so that it can be matched relative a position of the second cranial reference module 205-R.

The first cranial reference unit, the second cranial reference unit, or both the first and second cranial reference units can include a kinematic mount 205 as described above.

Figure 3:
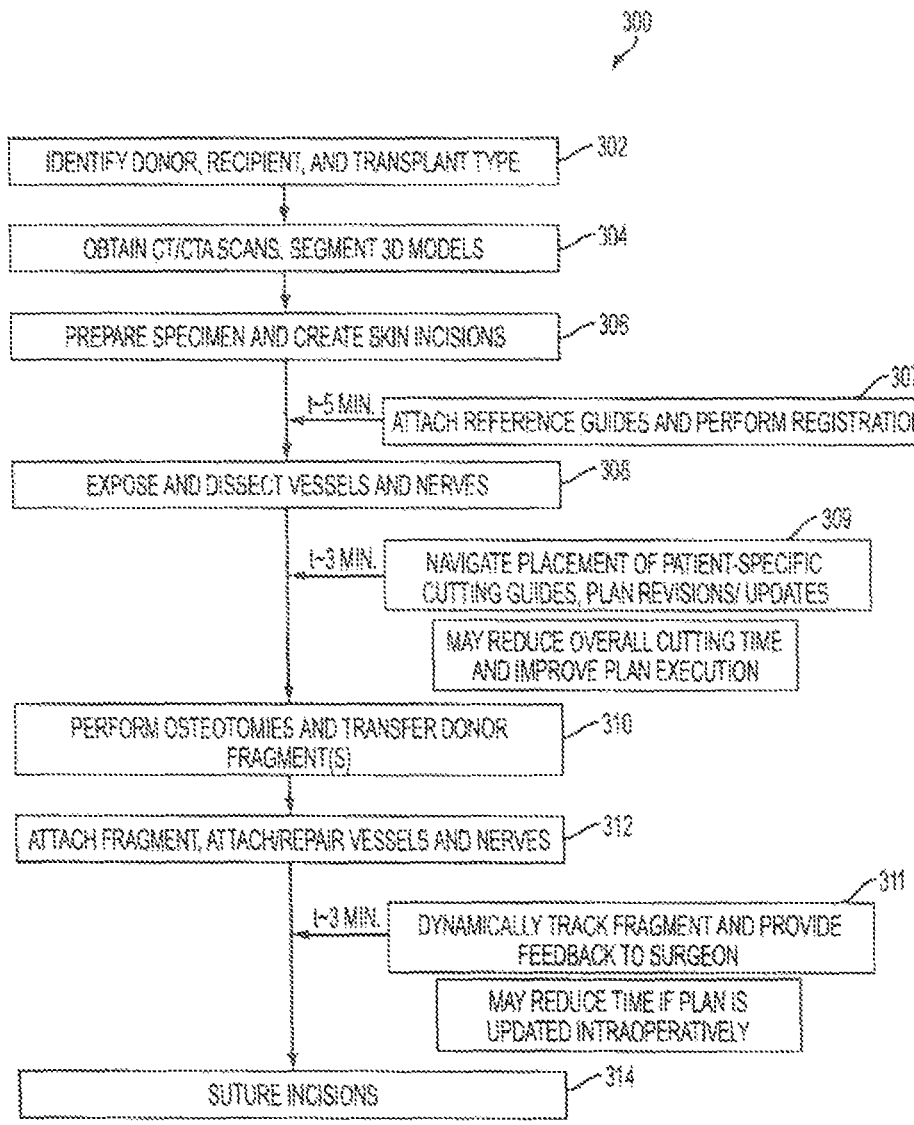
FIG. 3 is a flow chart depicting a procedure associated with use of the surgical system, for example, the surgical system of FIGS. 2A-2C.

Using the system of FIGS. 2A-2G, it is possible to execute a surgical method, such as the surgical method described in FIG. 3. For example, in step 302 a donor, recipient and transplant type are identified. CT/CTA scans of both the donor and recipient are collected and 3D models are created in step 304. The donor and recipients are prepared for surgery with the creation of skin incisions in step 306. The method continues at 307 with attachment of reference guides and performing registration. For example, a first cranial reference unit can be attached to a donor skeleton, a first fragment reference unit can also be attached to the donor skeleton at a location that is different that of the first cranial reference unit. The locations of the first cranial reference unit and the first fragment reference unit can be tracked with a first tracker. 3D reconstructions of the donor skeleton can be constructed showing a first virtual cranial reference unit and first virtual fragment reference unit superimposed on the first 3D reconstruction at locations that correspond to relative positions of the first cranial reference unit and the first fragment reference unit.

A second cranial reference unit can be attached to a recipient skeleton. A second location of the second cranial reference unit can be tracked with a second tracker. A second 3D reconstruction of the recipient skeleton can be created with a second virtual cranial reference unit superimposed on the second 3D reconstruction at a location that corresponds to a location of the second cranial reference unit. At 308, vessels and nerves are dissected and exposed. At this stage, navigation of the patient-specific cutting guides can occur, with plan revision and updates provided periodically. For example, a first cutting guide, such as a patient-specific cutting guide according to the descriptions provided above, can be attached onto the donor skeleton at a preselected location such as that corresponding to a planned cut-plane. The location of the first cutting guide can be tracked with the first tracker. A first virtual cutting guide can be superimposed on the first 3D reconstruction at a location that corresponds to a location of the first cutting guide relative to the location of the first cranial reference unit or the location of the first fragment reference unit.

A first virtual fragment can be formed by segmenting the 3D reconstruction of the donor skeleton at a location adjacent to the first virtual cutting guide. The first virtual fragment can be superimposed on the second 3D reconstruction of the recipient skeleton.

At step 310, a surgeon can perform an osteotomy on the donor skeleton to remove the first fragment but cutting the skeleton along a cutting path defined by the first cutting guide. Upon transferring the removed skeletal fragment from the donor, the first cutting guide can be tracked, by the second tracker, for example, when the fragment is brought near the recipient for attachment. The surgeon can then navigate placement of the cutting guide as it is dynamically tracked at step 311, and will receive feedback from the system such as by referring to a first virtual fragment that is superimposed on the second 3D reconstruction to form a hybrid 3D reconstruction. At step 312, the first fragment can then be attached to the recipient skeleton via known surgical methods and the incisions can be sutured in step 314.

The step of superimposing the first virtual fragment on the second 3D reconstruction of the recipient skeleton can include performing an automated cephalometric computation for the hybrid reconstruction. In fact, the step of superimposing the first virtual fragment on the second 3D reconstruction can include providing a communications link between a first workstation on which the first 3D reconstruction is displayed and a second workstation on which the second 3D reconstruction is displayed, and initiating a data transfer protocol that causes the first workstation and the second workstation to send electronic signals through the communications link.

Surgical methods of the embodiments described above can also include attaching a second cutting guide at a preselected location on the recipient skeleton. The second cutting guide can also include features of the cutting guide described above.

For the surgical methods of embodiments described herein the donor skeleton can include a male skeleton or a female skeleton and the recipient skeleton comprises a female skeleton. Alternatively, the donor skeleton can include a male or female skeleton and the recipient skeleton can include a male skeleton.

Surgical methods of the embodiments can further include steps for assessing a size-mismatch between the donor skeleton and the recipient skeleton by measuring a dorsal maxillary interface between the first fragment and recipient skeleton. In an embodiment, the surgical method can include selecting a location of the first fragment onto the recipient skeleton that minimizes dorsal step-off deformity at the area of osteosynthesis.

In an embodiment, the first cutting guide, second cutting guide or both the first cutting guide and the second guide comprise concentric cutting guides.

Surgical methods of embodiments can further include mapping the vascular system on the facial anatomy of both the recipient and the donor and superimposing corresponding virtual representations of the vascular system and the facial anatomy onto the first 3D representation, such as shown in FIG. 4B

Surgical methods of embodiments can include a method for registration of a preoperative model, for example a model reconstructed from CT data, to donor and recipient anatomy. Such a method can include: creating a plurality of indentations on the donor skeleton, creating a plurality of virtual markers on the first 3D reconstruction of the donor skeleton corresponding to the locations of the indentations on the donor skeleton, placing a trackable object on at least one of the plurality of indentations, and determining whether a subsequent location of the virtual markers is within a predetermined tolerance relative to an actual subsequent location of the indentations.

EXAMPLES

Example 1

Figure 9A:
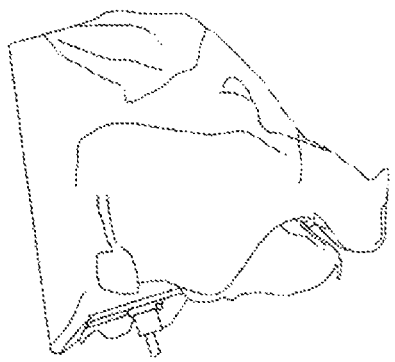
FIG. 9A-9D include photographs and renderings showing exemplary surgical results according to embodiments.
Figure 9B:
Figure 9C:
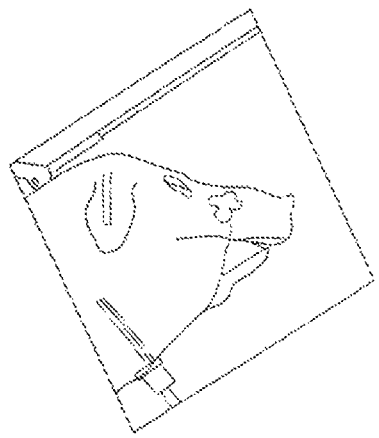
Figure 9D:
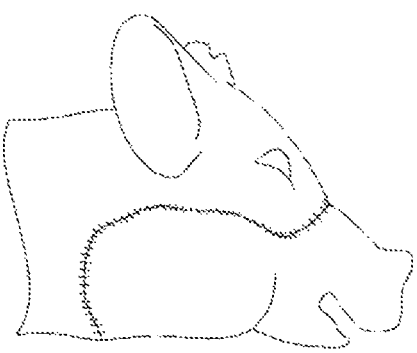

Live transplant surgeries (n=2) between four size-mismatched swine investigated whether or not an embodiment could actually assist a surgical team in planning and in executing a desired surgical plan. As shown in FIGS. 9A-9B, the first live surgery confirmed the proposed utility of overcoming soft and hard tissue discrepancies related to function and aesthetics. The final occlusal plane within the first recipient was ideal and consistent with the virtual plan as seen on lateral cephalogram as shown in FIG. 10C. Pre-operative functional predictions of donor-to-recipient occlusion were realized based on cephalometric analyses as shown in FIG. 9C performed both before and after surgery. Soft tissue inconsistencies of the larger-to-smaller swine scenario were also reduced following the predicted movements of face, jaw and teeth as shown in FIG. 10D.

The second live surgery showed improved success as compared to its predecessor due to surgeon familiarity and technology modifications. System improvements and growing comfort of the surgeons led to reduced operative times for both donor and recipient surgeries. Overall the surgical time reduced from over 14 hours to less than 8 hours due to improved surgical workflow and increased comfort with a system of an embodiment.

Based on the results obtained in the live and plastic bone surgeries, the functions associated with setting up a system of an embodiment (attaching references, performing registration, attaching cutting guides) adds about 11 minutes to the total length of surgery.

Figure 11A:
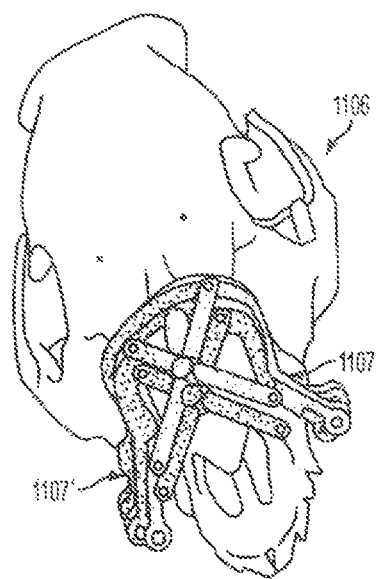
FIGS. 11A-11B are "on screen" images displayed by an imaging sub-system of a surgical system of the embodiments. The images depict an ideal location of a cutting guide versus actual position and an actual inset position of donor alloflap for aesthetic, dental and skeletal relation in size-mismatched donors due to anterior translation of cutting guide.
Figure 11B:
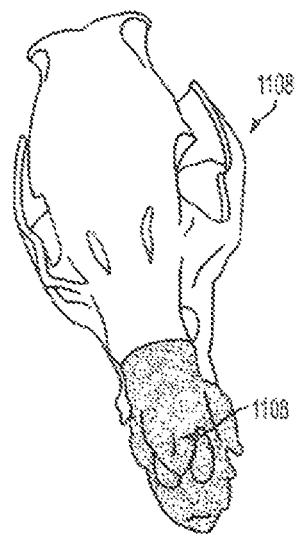

The system also recorded information, such as rendering information which can be stored in a storage medium of a workstation, relating the donor fragment 1002 to the recipient 1010 qualitatively as shown by color mismatch 1004, which matched the post-operative CT data as shown in FIG. 10. The recipient cutting guide 1107' was not placed as planned 1107, however, due to an unexpected collision between cranial reference mount and recipient cutting guide as shown in FIGS. 11A-11B. In this case, there was anterior translation of the cutting guide (toward the tip of the swine's snout) by approximately 4 cm.

Overall, the donor 1106 and recipient craniums (n=4) 1108 were registered successfully to the reference bodies for both live surgeries. The model to patient registration error across the surgeries was 0.6 (+/−0.24) mm. The cutting guide designs of the embodiments proved highly useful in carrying out the planned bone cuts, which compensated for size-mismatch discrepancies between donor and recipient. Marking spheres fixated to the guides allowed real-time movement tracking and "on-table" alloflap superimposition onto the recipient thereby allowing visualization of the final transplant result.

Example 2

Female and male donor heads (n=2), double-jaw, Le Fort III-based alloflaps were harvested using handheld osteotomes, a reciprocating saw, and a fine vibrating reciprocating saw. Both osteocutaneous alloflaps were harvested using a double-jaw, Le Fort III-based design (a craniomaxillofacial disjunction), with preservation of the pterygoid plates, incorporating all of the midfacial skeleton, complete anterior mandible with dentition, and overlying soft tissue components necessary for ideal reconstruction.

Prior to transplantation, both scenarios were completed virtually given the gender-specific challenges to allow custom guide fabrication as shown in panels A-H of FIG. 12. Once assimilated, the donor orthognathic two-jaw units were placed into external maxilla-mandibular fixation (MMF) using screw-fixated cutting guides to retain occlusal relationships during the mock transplants as shown in panels A-D of FIG. 13.

Figure 14A:
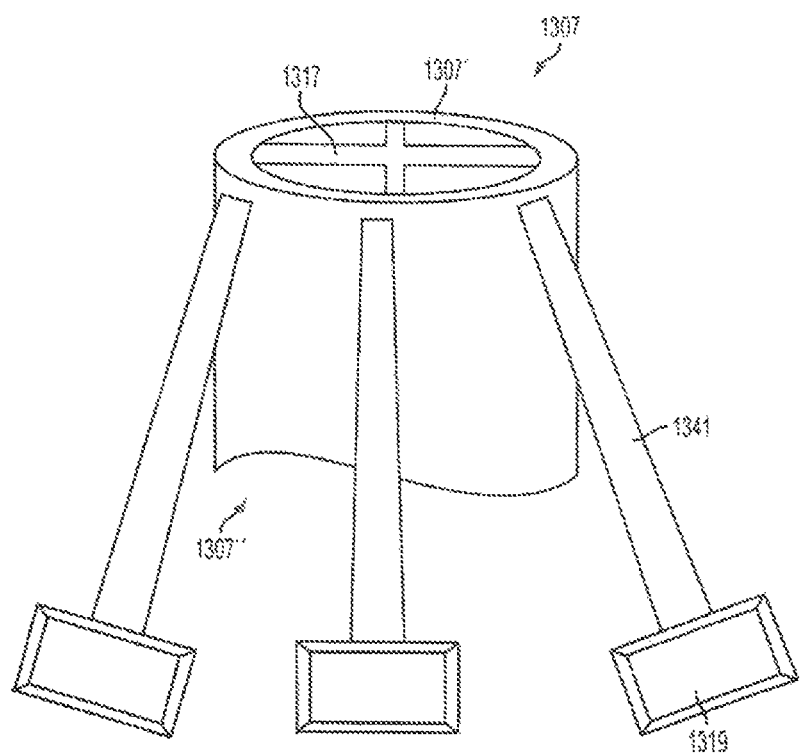
FIG. 14A illustrates a perspective view of a variation of a cutting guide, for example, a variation of the cutting guide of FIG. 13.
Figure 14B:
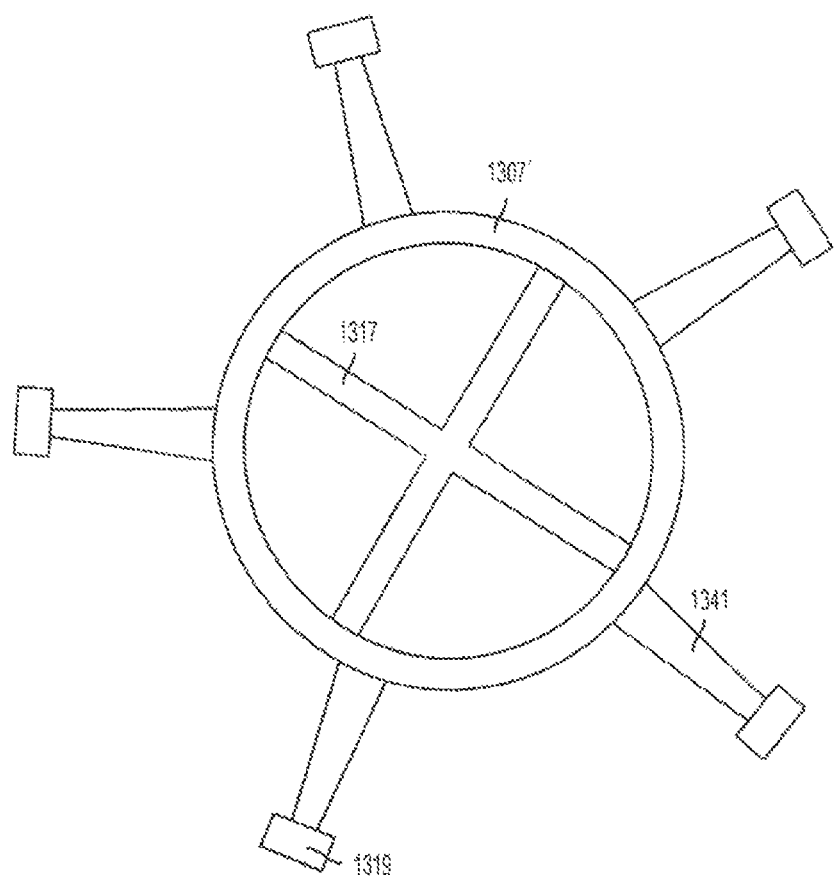
FIG. 14B illustrates a top view of a variation of a cutting guide, for example, a variation of the cutting guide of FIG. 13.

As shown in FIGS. 13, 14A-14B, an embodiment of a cutting guide 1307 can include a frame 1307' with at least one attachment surface 1319, for example 1 to 6 attachment surfaces, configured for attaching the cutting guide to a skeletal feature. The cutting guide can include a navigation surface 1317 (not shown in FIG. 13) connected to the frame. The navigation surface can include a reference geometry that can be tracked by a tracker, for example, via IR optical tracking. The at least one attachment surface 1319 can include a contoured surface corresponding to contours of portions of the skeletal feature, for example, such as the contours of a skeletal feature that intersect a planned-cut plane as indicated by 1319' in FIG. 12. The at least one attachment surface 1319 can be detachably connected to a skeletal feature. The at least one attachment surface 1319 can be detachably connected to an attachment guide 1341. The attachment guide 1341 can be detachably connected to a portion of the frame 1307'. For example, attachment guides 1341 can be detachably connected via slots integrated into frame 1307', or held in place against frame 1307 with screws or the like. In another embodiment, attachment guides 1341 are formed as portions of frame 1307' but can be removed. The frame can have a ring-like shape (as shown in FIG. 13) or can have a cylinder-like shape (as shown in FIG. 14A). Frame 1307' having a cylinder like shape can have a bottom surface 1307" that rests against a patient's soft tissue to provide support for the frame.

For example, during a surgical procedure, 3D reconstructions of portions of a donor skeleton are created. Planned cutting planes are selected and a cutting guide with attachment surfaces having a contoured surface corresponding to contours of portions of the skeletal feature, for example, such as the contours of a skeletal feature that intersect a planned-cut plane, is designed. The designed cutting guide is manufactured via, for example, an additive manufacturing process. The designed cutting guide with an integrated navigation surface is attached to the patient. For example, the cutting guide can be designed such that it has a snap-on fit over the skeletal feature, which can be further secured to the skeletal feature with set screws. A surgeon removes a donor skeletal fragment with the cutting guide attached to the fragment. The donor skeletal fragment is then attached to the recipient. As the donor skeletal fragment is attached to the recipient, the attachment surfaces are removed from the donor fragment. For example, each of the attachment guides 1341 with a corresponding attachment surface 1319 can be detached from the frame 1307'. As this occurs, a cylindrical shaped frame 1307' has a bottom surface 1307" that rests against the soft tissue of the patient to provide stability for the remaining portions of the cutting guide and to hold the navigation surface 1317' in place.

While the invention has been illustrated respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function.

For example, the embodiments described herein can be used for navigation and modeling for osteotomy guidance during double-jaw face transplantation, single-jaw maxillofacial transplantation, and any other neurosurgical, ENT/head and neck surgery, or oral maxillofacial surgical procedure alike.

Embodiments described herein can include platform for preoperative planning and intraoperative predictions related to soft tissue-skeletal-dental alignment with real-time tracking of cutting guides for two mismatched jaws of varying width, height and projection. Additional safeguards, such as collection of confidence points, further enable intraoperative verification of the system accuracy. This, in addition to performing real-time plan verification via tracking and dynamic cephalometry, can considerably increase the robustness of the systems described herein. Moreover, systems of embodiments can include a modular system that allows additional functionality to be continually added.

Embodiments described herein can include an approach for resolving conflicts in case of position discrepancies between the placement of the guide and the guide position prompted by the navigation software. Such discrepancy may be due to either the guide (soft tissue interference, iatrogenic malpositioning, changes since the CT data was obtained or imperfections in cutting guide construction/printing), and/or the navigation system (e.g. registration error, or unintended movement of the kinematic markers). To resolve these source(s) of discrepancy, four indentations can be created on a bone fragment (confidence points) where a reference kinematic marker is attached. At any time during an operation, a surgeon can use a digitizer and compare the consistency of the reported coordinates of the indentations via navigation to their coordinates with respect to a virtual computer model.

Embodiments described herein can include a system that provides real-time dynamic cephalometrics and masticatory muscle biomechanical simulation for both planning and intraoperative guidance to ensure ideal outcomes in craniomaxillofacial surgery.

Figure 12D:
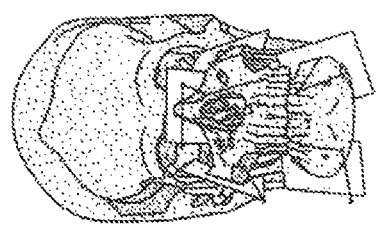
FIG. 12 illustrates virtual osteotomy and planned cut plane placement on virtual representations of a skeletal feature.
Figure 12C:
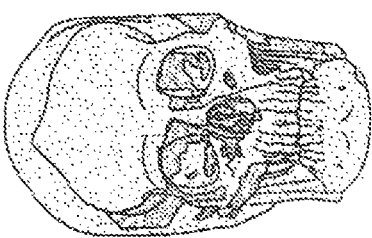

FIG. 15 is an example method of a computer-implemented method for computer-assisted planning of a transplant surgery 1500, according to the present teachings. At 1505, the method can include obtaining a computer-readable representation of a donor skeletal fragment, as shown in FIG. 12A. The computer-readable representation of a donor skeletal fragment can be created based, at least in part, on one or more medical imaging techniques. Also, the computer-readable representation of the donor skeletal fragment can comprise one or more of: a vascular model or a neural model of the donor skeletal fragment, as shown in FIG. 4B. The donor skeletal fragment can be from the same patient or from another patient or source.

Figure 12B:
Figure 12A:
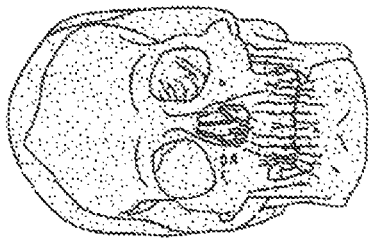

At 1510, the method can include obtaining a computer-readable representation of a recipient skeletal fragment, as shown in FIG. 12B. Similarly to FIG. 12A, the computer-readable representation of a donor skeletal fragment of FIG. 12B can be created based, at least in part, on one or more medical imaging techniques. Again, the computer-readable representation of the recipient skeletal fragment can comprise one or more of: a vascular model or a neural model of the recipient skeletal fragment, as shown in FIG. 4B.

In some aspects, the computer-readable representation of the recipient skeletal fragment and the donor skeletal fragment can comprises a segmented 3D reconstruction model. The segmented 3D model can be created using the one or more medical imaging techniques and a segmentation algorithm. For each voxel of the segmented 3D reconstruction model of the recipient skeletal fragment and the donor skeletal fragment, an associated anatomical attribute can be associated thereto to classify an anatomy for which each voxel represents. For example, each voxel may include anatomical characteristic consistent with, but are not limited to, bone or soft tissues, such as cartilage, neural and/or vascular structures.

Figure 12H:
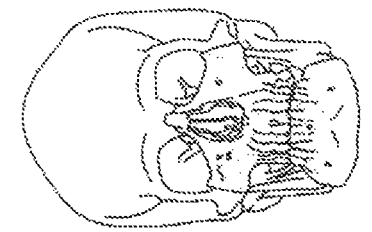
Figure 12G:
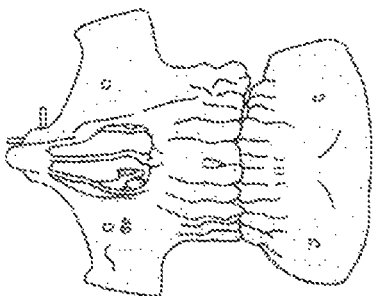
Figure 12F:
Figure 12E:
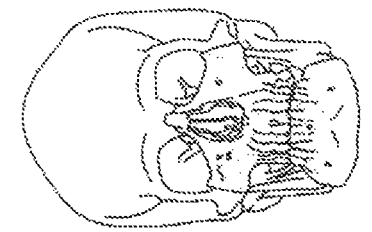
Figure 13A:
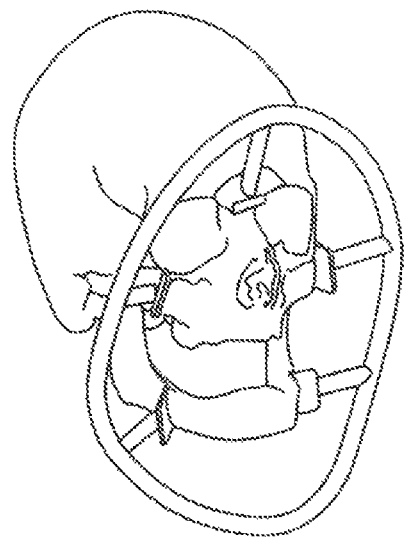
FIG. 13 shows virtual placement of a cutting guide alongside photographs of an actual placement.
Figure 13B:
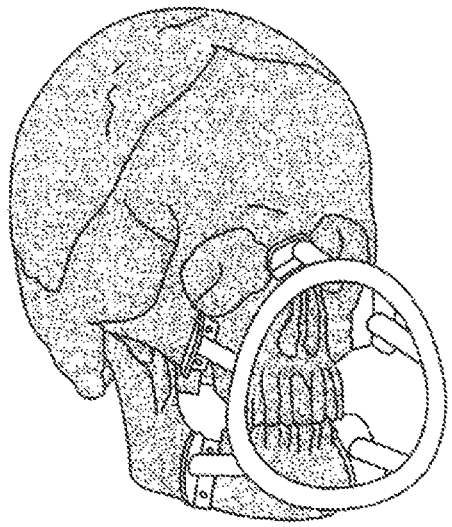
Figure 13C:
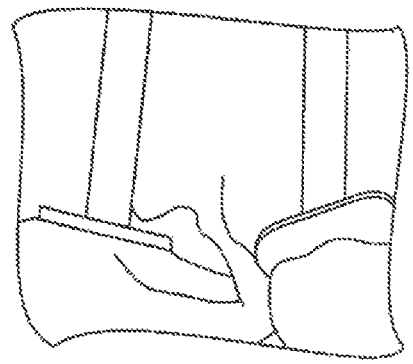
Figure 13D:
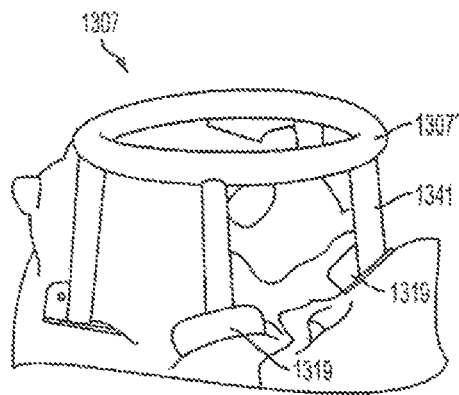

At 1515, the method can include determining one or more surgical cutting planes on the computer-readable representation of the donor skeletal fragment from which a portion of the donor skeletal fragment from the computer-readable representation of the donor skeletal fragment will be harvested. For example, as shown in FIGS. 12D and 12E, cutting planes 1319' are shown on the computer-readable representations. In some aspects, the cutting planes may be associated with or coincide with one or more fracture planes commonly encountered in LeFort-type fractures, such as LeFort I, II, and/or III fractures. Once determined, the one or more surgical cutting planes can be positioned onto the computer-readable representation of the donor skeletal fragment.

At 1520, the method can include determining one or more virtual cutting guides based on the one or more surgical cutting planes to be attached to the computer-readable representation of the donor skeletal. The one or more cutting guides can be used to assist the surgeon in carrying out the correct surgical incision based, at least in part, on the one or more surgical cutting planes. At 1525, the method can include performing a virtual osteotomy to separate the portion of the donor skeletal fragment from the computer-readable representation of the donor skeletal fragment from a remainder portion of the donor skeletal fragment based on a position of the one or more virtual cutting guides that are attached to the computer-readable representation of the donor skeletal fragment. For example, as shown at 217-D in FIG. 8A, cutting guides can be used to assist the surgeon during the planning and actual surgery, in correctly removing the donor skeletal fragment based, at least in part, on the surgical cutting planes that were determined.

At 1530, the method can include positioning the donor skeletal fragment within a transplant region of the recipient skeletal fragment. For example, as shown in FIGS. 12G and 12H, the donor skeletal fragment is shown positioned onto the recipient skeletal fragment. In some aspects, movement of the donor skeletal fragment of the computer-readable representation can be tracked during the positioning. The tracking can be performed by identifying a set of cephalometric landmarks associated with the hybrid computer-readable representation. A set of cephalometric metrics can then be calculated for the set of cephalometric landmarks that are identified. The surgeon can then determine whether an acceptable result of the surgery being planned has been achieved based, at least in part, on the set of cephalometric metrics that are calculated. The set of cephalometric landmarks comprise one or more of: Gonion ("Go"), Nasion ("N"), A point ("A"), B point ("B"), Sella ("S"), Menton ("M"), left/right Zygoma ("ZY"), Os occipital ("OCC"). Other cephalometric landmarks can also be used.

At 1535, the method can include creating a hybrid computer-readable representation comprising the recipient skeletal fragment and the portion of the donor skeletal fragment during or after the positioning. At 1540, the method can include providing the hybrid computer-readable representation as an output. FIG. 12H shows an example of the hybrid computer-readable representation. As the donor fragment is positioned around the recipient, the hybrid computer-readable representation and the output can be updated based, at least in part, on the movement being tracked. Also, during this planning process, the one or more surgical cutting planes or cutting guides can be modified based on whether the surgeon considers the positioning and placement of the donor skeletal fragment on the recipient an acceptable result. This process can be aided by comparing the set of cephalometric metrics that were calculated with a set of baseline cephalometric metrics. Additionally, the updates and/or real-time feedback can be in a form such as a change in appearance of a visual indicator on a hybrid model as the donor skeletal fragment is mated with the recipient skeletal fragment, as is shown and described in relation to FIGS. 2B, 2C, 11A, and 11B, where the color is caused to change from one color to another color. For example in FIGS. 2B and 2C, the color changes from red to green when the donor skeletal fragment is properly mounted onto the recipient. By way of one example, the donor skeletal fragment can comprise at least a maxilla or mandible and the real-time feedback that is provided can comprise providing a visual indication as to how well one or more teeth of the hybrid maxilla-mandible combination match.

Figure 16:
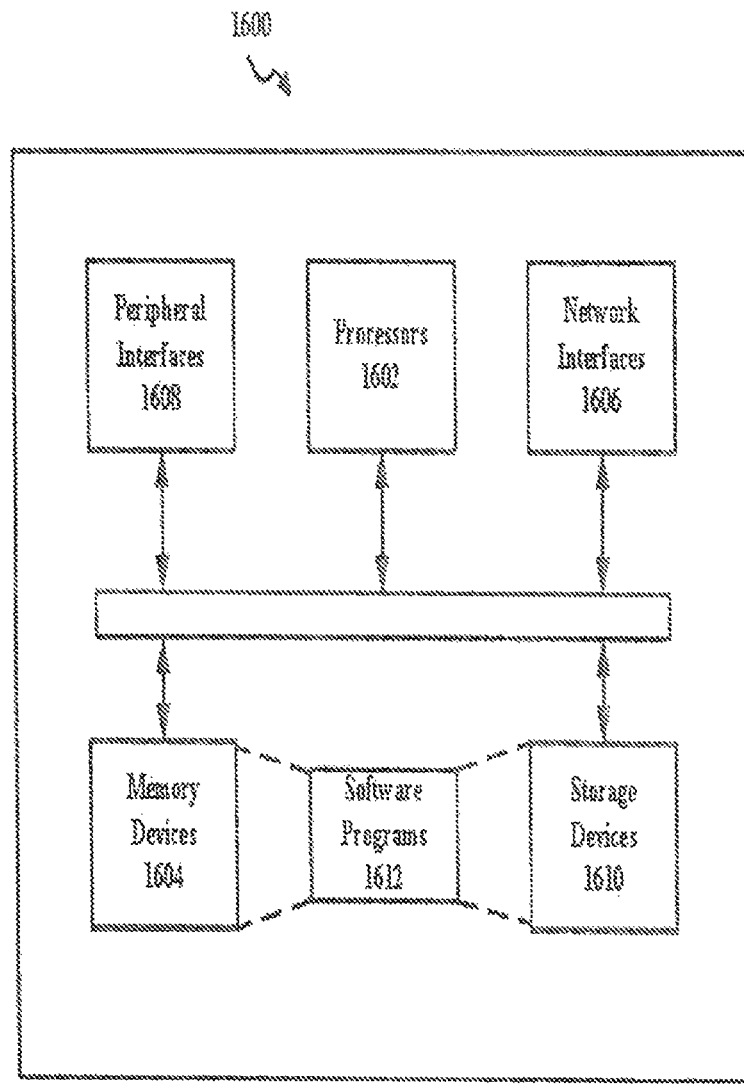
FIG. 16 illustrates an example schematic view of such a computing or processor system that can perform the methods disclosed herein, according to an embodiment.

FIG. 16 illustrates a schematic view of such a computing or processor system 1600, which can include the computers 215-D and 215-R, according to an embodiment. The processor system 1600 may include one or more processors 1602 of varying core configurations (including multiple cores) and clock frequencies. The one or more processors 1602 may be operable to execute instructions, apply logic, etc. It will be appreciated that these functions may be provided by multiple processors or multiple cores on a single chip operating in parallel and/or communicably linked together. In at least one embodiment, the one or more processors 1602 may be or include one or more GPUs.

The processor system 1600 may also include a memory system, which may be or include one or more memory devices and/or computer-readable media 1604 of varying physical dimensions, accessibility, storage capacities, etc. such as flash drives, hard drives, disks, random access memory, etc., for storing data, such as images, files, and program instructions for execution by the processor 1602. In an embodiment, the computer-readable media 404 may store instructions that, when executed by the processor 1602, are configured to cause the processor system 1600 to perform operations. For example, execution of such instructions may cause the processor system 1600 to implement one or more portions and/or embodiments of the method described above.

The processor system 1600 may also include one or more network interfaces 1606. The network interfaces 1606 may include any hardware, applications, and/or other software. Accordingly, the network interfaces 1606 may include Ethernet adapters, wireless transceivers, PCI interfaces, and/or serial network components, for communicating over wired or wireless media using protocols, such as Ethernet, wireless Ethernet, etc.

The processor system 1600 may further include one or more peripheral interfaces 1608, for communication with a display screen, projector, keyboards, mice, touchpads, sensors, other types of input and/or output peripherals, and/or the like. In some implementations, the components of processor system 1600 need not be enclosed within a single enclosure or even located in close proximity to one another, but in other implementations, the components and/or others may be provided in a single enclosure.

The memory device 1604 may be physically or logically arranged or configured to store data on one or more storage devices 1610. The storage device 1610 may include one or more file systems or databases in any suitable format. The storage device 1610 may also include one or more software programs 1612, which may contain interpretable or executable instructions for performing one or more of the disclosed processes. When requested by the processor 1602, one or more of the software programs 1612, or a portion thereof, may be loaded from the storage devices 1610 to the memory devices 1604 for execution by the processor 1602.

Those skilled in the art will appreciate that the above-described componentry is merely one example of a hardware configuration, as the processor system 1600 may include any type of hardware components, including any necessary accompanying firmware or software, for performing the disclosed implementations. The processor system 1600 may also be implemented in part or in whole by electronic circuit components or processors, such as application-specific integrated circuits (ASICs) or field-programmable gate arrays (FPGAs).

The foregoing description of the present disclosure, along with its associated embodiments and examples, has been presented for purposes of illustration only. It is not exhaustive and does not limit the present disclosure to the precise form disclosed. Those skilled in the art will appreciate from the foregoing description that modifications and variations are possible in light of the above teachings or may be acquired from practicing the disclosed embodiments.

ADDITIONAL EMBODIMENTS

Osseointegrated Dental Implants

Patients with poor or missing dentition require dental implants to improve mastication. A popular modality with increasing indications include "osseointegrated dental implants". Osseointegrated dental implants can include, and may consist of, a two-piece permanent implant device, which is placed into either the maxilla or mandible skeleton with a power drill for placement and stability. A second piece, in the shape of a tooth for example, is scewed onto the secure base. An embodiments of the CAPE system described above can be used to provide the dentist or surgeon real-time cephalomteric feedback in an effort to restore ideal occlusion and predict optimized mastication with biomechanical predictions—as similar to maxillofacial transplantation. As such, the dentist or surgeon placing them needs to know the bone stock quality of the jaw(s) and angle to place the framework. In summary, the CAPE system described above may be applied to this specialty.

Osseointegrated Craniofacial Prosthetics

Patients with severe cranial or facial disfigurement may be poor surgical candidates due to overwhelming co-morbities and/or because of an accompanying poor prognosis. Therefore, to help return these patients into society, some use craniofacial prosthetics as a way to restore "normalcy". Application of these three-dimensional prosthetics replacing absent craniofacial features (ie. nose, eye, etc) may either be hand-molded/painted by an anaplastologist or printed with 3D technology by a prostheticraniofacialian. Either way, in an embodiment, the CAPE system described above can provide a one-stop solution for patients requiring alloplastic and/or bioengineered prosthetic reconstruction for large craniomaxillofacial deformities. The craniofacial implants can be tracked as similar to a donor face-jaw-teeth segment described above. For example, pre-placement images of the prosthetic could be fabricated, and surgical plans could be optimized since these appliances are placed with osseointegrated devices as similar to dental implants described above—with rigid plates and screws. As such, the surgeon placing them needs to know the bone stock quality and angle to place the framework, and also needs to known with visual feedback as to the ideal position in three-dimensional space. In summary, the CAPE system described here may be applied to this specialty.

Craniomaxillofacial Trauma Reconstruction

Patients suffering from acute or chronic facial disfigurement is a common type seen by the craniomaxillofacial surgeon. Both penetrating and/or blunt trauma may cause significant damage to the underlying facial skeleton. As such, in an embodiment, the CAPE system technology described herein allows the surgeon to assess and optimize bone fragment reduction and reconstruction with real-time feedback. In addition, fractures affecting the jaws can be aided by real-time cephalometrics in hopes to restore the patient back to their pre-trauma angle/measurements (as a way to assure proper occlusion). Navigation, as described above in an embodiment of the CAPE system, can be exceptionally helpful for orbit fractures around the eye or cranial fractures around the brain, since the nerve anatomy is delicate and consistent—which makes it applicable to the CAPE system. In summary, a surgeon (including the likes of a Plastic surgeon, ENT surgeon, oral/OMFS surgeon, oculoplastic surgeon, neurosurgeon) reducing craniofacial fractures needs to know the bone stock quality remaining, where plates/screws are best placed, and the optimal plan prior to entering the operating room. Therefore, the CAPE system described within may be applied to this area as well.

Neurosurgical Procedures

Neurosurgeons frequently perform delicate craniotomies for access for brain surgery. Currently, there are several navigational systems available. However, none of the conventional systems include features described in the embodiments of the CAPE platform as described above. That is, the conventional systems lack the ability to assist both pre-operatively with planning AND with intra-operative navigation for execution assistance. In addition, the current neurosurgery systems require the head to be placed in antiquidated "bilateral skull clamp pins" during the entire surgery. This means that before each neurosurgery procedure starts, a big 3-piece clamp is crunched onto the skull of the patient to make sure the head does not move during surgery, particularly to allow for use of the conventional navigation systems. However, embodiments of the CAPE system, such as those described above, use a small, modified rigid cranial reference mount which removes the need for using a big, bulky clamp from the field and allows the surgeon to rotate the patient's head if and when needed. To a craniofacial plastic surgeon, who often is consulted to assist with simultaneous scalp reconstruction, elimination/removal of such pins from the surgical field is a huge advantage. For example, elimination of the pins makes scalp reconstruction in the setting of neurosurgery much safer since the pins aren't present to hold back mobilization and dissection of the nearby scalp—which is needed often for complex closure. It also, reduces the risk of surgical contamination since the current setup with pins is bulky and makes surgical draping and sterility much more difficult and awkward. A small cranial mount as part of the CAPE system is a huge advancement for the field. As such, the CAPE system described herein may be applied to neurosurgical procedures as well.

Congenital Deformity Correction

Unfortunately, newborns are commonly born with craniofacial deformities to either maternal exposure or genetic abnormalities. As such, they may have major development problems with their skeleton and the overlying structures (eyes, ears, nose) may therefore appear abnormal. In addition, newborns may suffer from craniosynostosis (premature fusing of their cranial sutures) which causes major shifts in the shape of their head at birth. In an embodiment, the CAPE system described above, can be utilized to address such congenital deformities, irrespective of etiology. For example, if a 16 year old needs to have major Le Fort surgery to move the central facial skeleton into better position forward to improve breathing, mastication, and appearance, use of the CAPE system technology for both pre- and intra-operatively provides a huge advancement for the field.

Head/Neck and Facial Reconstruction (ENT Surgery)

Head and neck surgeons in the specialty of Otolarygology (ENT) are frequently reconstructing facial skeletons. Reasons include post-tumor resection, facial trauma, aesthetic improvement, congenital causes and/or functional improvement (nose, mouth, eyes, etc). Therefore, this specialty would greatly benefit from use of the CAPE system technology described herein. For example, in an embodiment, use of the CAPE system can help a wide range including such instances as post-trauma fracture reduction/fixation, free tissue transfer planning and execution (ie. Free flap reconstruction with microsurgical fibula flaps for large bone defects where the leg bone receives dental implants for jaw reconstruction), smaller jaw reconstruction cases with implant materials, and/or anterior skull base reconstructions with neurosurgery following tumor resection. This specialty is very diverse, and therefore the CAPE system's easy adaptability can help make it greatly valuable to this group of surgeons.

Orthognathic Surgery

Orthognathic surgery describes any of surgical procedure type moving the jaw and/or jaw-teeth segments. This is most commonly performed by either oral surgeons, oral-maxillofacial surgeons (OMFS), or plastic surgeons. It is done currently both in the hospital as an insurance case or in the outpatient setting for a fee-for-service. It may be indicated for enhanced mastication, improved aesthetics, and/or both reasons. Having the ability to plan and predict jaw movements based on biomechanical muscle (ie. External) forces will be immensely valuable to this field. In an embodiment, surgeons can utilize the CAPE system described above to predict functional jaw movements both at time of surgery and after surgery (1, 5, 10, 20 years post-op). In addition, in an embodiment, a surgeon can utilize the CAPE system to provide real-time cephalometric feedback, which provides an advancement not seen in the conventional systems. In comparison, for the last several centuries, oral surgeons have used splints fabricated in the dental lab pre-operatively for assistance in the operating room—to help confirm dental alignment as planned. This takes time (4-6 hours to make by hand), effort (can be done virtually nowadays but is very expensive) and money. In contrast to the conventional systems, Surgeons utilizing the CAPE system, such as an embodiment described above, can go to the operating room with pre-fabricated cutting guides and tracking instruments, cut the jaws where planned, and then match the teeth on the table based on real-time cepholmetric feedback and biomechanical jaw simulation to predict post-operative mastication—unlike ever before. For example, use of the CAPE system will allow surgeons to know instantaneously if the aesthetic and functional angles/measurements are ideal and where they should be. In addition, the CAPE system is able to supply palatal cutting guides and pre-bent metal fixation plates (as opposed to the conventional methods that require handbending each plate for proper shape). In summary, the CAPE system will be a "game-changer" for orthognathic surgery.

"Computer-Assisted Cranioplasty"

At least some embodiments described herein can be used for the immediate surgical repair of large cranial defects (>5 $cm^2$). For example, embodiments described herein may be used for designing, forming and implanting customized craniofacial implants following benign/malignant skull neoplasm (tumor) resection (i.e. referred to as "single-stage implant cranioplasty"). Currently, it is challenging to reconstruct such patients with pre-fabricated implants using conventional methods since the actual size/shape of the defect site is unknown until the tumor is removed. Accordingly, use of a computer-assisted surgical system of an embodiment may significantly reduce the intraoperative time used for reshaping/resizing the customized implant. For example, embodiments provide visualization related to the tumor, the resulting skull defect, and the reshaped implant for exact positioning. In other words, in an embodiment, a Computer-Assisted Planning and Execution (CAPE) system that can be utilized for Le Fort-based, Face-Jaw-Teeth transplantation may also be used for improving both the pre-operative planning and intra-operative execution of single-stage implant cranioplasties. Cranioplasties may be performed to reconstruct large defects following stroke, trauma, aneurysmal bleeding, bone flap removal for infection, and oncological ablation. However, oncological defects are commonly reconstructed with "off-the-shelf" materials, as opposed to using a pre-fabricated customized implant—simply because the exact defect size/shape is unknown. With this in mind, embodiments described herein include a computer-assisted algorithm that may allow surgeons to reconstruct tumor defects with pre-customized cranial implants (CCIs) for an ideal result.

Nearly 250,000 primary brain tumors/skull-based neoplasms are diagnosed each year resulting in a range of 4500-5000 second-stage implant cranioplasties/year. Unfortunately, the common tumor defect cranioplasty is reconstructed with on-table manipulation of titanium mesh, liquid polymethylmethacrylate (PMMA), liquid hydroxyapatitie/bone cement (HA) or autologous split-thickness calvarial bone grafts (ref), which forces the surgeon to shape/mold these materials to an approximate size/shape. Expectantly, this results in some form of craniofacial asymmetry and a post-operative appearance which is suboptimal. Furthermore, the difficult shaping process may take several hours—which in turn increases anesthesia, total blood loss, risk for infection, morbidity, and all costs associated with longer operative times. Therefore, there is significant opportunity to extend this CAPE to thousands of patients.

In 2002, the advent of computer-aided design and manufacturing (CAD/CAM) was used for the first time to pre-emptively match the contralateral, non-operated skull for ideal contour and appearance, which provided for the use of CCIs. However, cranioplasties with such CCIs can only be performed as "second stage" operations during which a clinician, such as a surgeon, ensures that the CCI fits perfectly into the skull defect. Recent developments have demonstrated the feasibility of CCIs for "single-stage cranioplasty", but this involves using a handheld bur to shave down the pre-fabricated implant artistically. However, challenges m both assessing and predicting each tumor-resection deformity pre-surgery still limits the applicability of CCIs in this patient population. For example, challenges such as 1) unknown exact tumor size, 2) unknown growth from time of pre-op CT scan-to-actual day of surgery, and 3) the unknown resection margins needed to minimize local recurrence. For these cases, the CCI would need to be reshaped/resized intraoperatively from a size slightly larger than expected—which is a process that may take several (2-4) hours. However, there are no established planning and execution systems available to assist these single-stage reconstructions. Accordingly, embodiments described herein may be used by surgeons in performing single-stage cranioplasty following oncological resection. In other words, embodiments include algorithms for real-time updates related to single-stage customized implant cranioplasty. For example, in an embodiment, there is a Computer-Assisted Planning and Execution (CAPE) system, which is a SINGLE, seamless platform capable of being used for both planning (pre-op use) and navigation (intra-op use) which overcomes the limitations of conventional systems that do either one or the other. In addition, embodiments include novel hardware such as trackable cutting guides and rigid cranial reference mount. The CAPE architecture will provide reconstructive surgeons all the necessary algorithms for real-time updates related to single-stage customized implant cranioplasty.

TABLE 1

Comparison of CAPE and Competitive Solutions

| | Innovation Group | Brainlab | Med Surg Services | Medtronic | Paritic | Praxim/ Ortho Surg | Siemens | Smith & Nephew | Stryker | Zimmer | CAPE |
|---|---|---|---|---|---|---|---|---|---|---|---|
| Virtual Planning | ✓ | X | ✓ | X | X | X | X | X | X | X | ✓ |
| Navigation | ✓ | ✓ | ✓ | ✓ | ✓ | ✓ | ✓ | ✓ | ✓ | ✓ | ✓ |
| Real time cephalometrics | X | X | X | X | X | X | X | X | X | X | ✓ |
| Trackable cutting guides | X | X | X | X | X | X | X | X | X | X | ✓ |
| Biomechanical Simulation | X | X | X | X | X | X | X | X | X | X | ✓ |
| Multiple stations | X | X | X | X | X | X | X | X | X | X | ✓ |

Furthermore, to the extent that the terms "including", "includes", "having", "has", "with", or variants thereof are used in either the detailed description and the claims, such terms are intended to be inclusive in a manner similar to the term "comprising." As used herein, the phrase "one or more of", for example, A, B, and C means any of the following: either A, B, or C alone; or combinations of two, such as A and B, B and C, and A and C; or combinations of three A, B and C.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method for computer-assisted planning of a transplant surgery, the method comprising:

creating a computer-readable representation of a donor skeletal fragment based on one or more medical imaging techniques, wherein the computer-readable representation of the donor skeletal fragment comprises one or more of: a vascular model or a neural model of the donor skeletal fragment;

creating a computer-readable representation of a recipient skeletal fragment based on one or more medical imaging techniques, wherein the computer-readable representation of the recipient skeletal fragment comprises one or more of: a vascular model or a neural model of the recipient skeletal fragment, wherein the computer-readable representation of the recipient skeletal fragment and the donor skeletal fragment comprises a segmented 3D reconstruction model that is created using the one or more medical imaging techniques and a segmentation algorithm, and wherein each voxel of the segmented 3D reconstruction model of the recipient skeletal fragment and the donor skeletal fragment comprises an associated anatomical attribute that classifies an anatomy for which each voxel represents;

determining one or more surgical cutting planes on the computer-readable representation of the donor skeletal fragment from which a portion of the donor skeletal fragment will be harvested from the computer-readable representation of the donor skeletal fragment;

determining one or more virtual cutting guides based on the one or more surgical cutting planes to be attached to the computer-readable representation of the donor skeletal fragment;

performing a virtual osteotomy to separate the portion of the donor skeletal fragment from the computer-readable representation of the donor skeletal fragment from a remainder portion of the donor skeletal fragment based on a position of the one or more virtual cutting guides that are attached to the computer-readable representation of the donor skeletal fragment;

positioning the donor skeletal fragment within a transplant region of the recipient skeletal fragment;

creating a hybrid computer-readable representation comprising the recipient skeletal fragment and the portion of the donor skeletal fragment during or after the positioning; and providing the hybrid computer-readable representation as an output.

2. A computer-implemented method for computer-assisted planning of a transplant surgery, the method comprising:

obtaining a computer-readable representation of a donor skeletal fragment;

obtaining a computer-readable representation of a recipient skeletal fragment;

determining one or more surgical cutting planes on the computer-readable representation of the donor skeletal fragment from which a portion of the donor skeletal fragment will be harvested from the computer-readable representation of the donor skeletal fragment;

determining one or more virtual cutting guides based on the one or more surgical cutting planes to be attached to the computer-readable representation of the donor skeletal fragment;

performing a virtual osteotomy to separate the portion of the donor skeletal fragment from the computer-readable representation of the donor skeletal fragment from a remainder portion of the donor skeletal fragment based on a position of the one or more virtual cutting guides that are attached to the computer-readable representation of the donor skeletal fragment;

positioning the donor skeletal fragment within a transplant region of the recipient skeletal fragment;

creating a hybrid computer-readable representation comprising the recipient skeletal fragment and the portion of the donor skeletal fragment during or after the positioning;

tracking movement of the donor skeletal fragment of the computer-readable representation during the positioning;

updating the hybrid computer-readable representation based on the movement being tracked; and providing the hybrid computer-readable representation as an output.

3. A computer-implemented method for computer-assisted planning of a transplant surgery, the method comprising:

obtaining a computer-readable representation of a donor skeletal fragment;

obtaining a computer-readable representation of a recipient skeletal fragment;

determining one or more surgical cutting planes on the computer-readable representation of the donor skeletal fragment from which a portion of the donor skeletal fragment will be harvested from the computer-readable representation of the donor skeletal fragment;

determining one or more virtual cutting guides based on the one or more surgical cutting planes to be attached to the computer-readable representation of the donor skeletal fragment;

performing a virtual osteotomy to separate the portion of the donor skeletal fragment from the computer-readable representation of the donor skeletal fragment from a remainder portion of the donor skeletal fragment based on a position of the one or more virtual cutting guides that are attached to the computer-readable representation of the donor skeletal fragment;

positioning the donor skeletal fragment within a transplant region of the recipient skeletal fragment;

creating a hybrid computer-readable representation comprising the recipient skeletal fragment and the portion of the donor skeletal fragment during or after the positioning; and providing the hybrid computer-readable representation as an output;

identifying a set of cephalometric landmarks associated with the hybrid computer-readable representation;

calculating a set of cephalometric metrics for the set of cephalometric landmarks that are identified;

determining an acceptable result of the surgery being planned based at least in part on the set of cephalometric metrics that are calculated; and updating at least one of the one or more surgical cutting planes or cutting guides based on the determination of acceptable result.

4. The computer-implemented method of claim 3, wherein the set of cephalometric landmarks comprise one or more of: Gonion ("Go"), Nasion ("N"), A point ("A"), B point ("B"), Sella ("S"), Menton ("M"), left/right Zygoma ("ZY"), Os occipital ("OCC").

5. A computer-implemented method for computer-assisted planning of a transplant surgery, the method comprising:

obtaining a computer-readable representation of a donor skeletal fragment;

obtaining a computer-readable representation of a recipient skeletal fragment;

determining one or more surgical cutting planes on the computer-readable representation of the donor skeletal fragment from which a portion of the donor skeletal fragment will be harvested from the computer-readable representation of the donor skeletal fragment;

determining one or more virtual cutting guides based on the one or more surgical cutting planes to be attached to the computer-readable representation of the donor skeletal fragment;

performing a virtual osteotomy to separate the portion of the donor skeletal fragment from the computer-readable representation of the donor skeletal fragment from a remainder portion of the donor skeletal fragment based on a position of the one or more virtual cutting guides that are attached to the computer-readable representation of the donor skeletal fragment;

positioning the donor skeletal fragment within a transplant region of the recipient skeletal fragment;

creating a hybrid computer-readable representation comprising the recipient skeletal fragment and the portion of the donor skeletal fragment during or after the positioning; and providing the hybrid computer-readable representation as an output;

identifying a set of cephalometric landmarks associated with the hybrid computer-readable representation;

calculating a set of cephalometric metrics for the set of cephalometric landmarks that are identified;

comparing the set of cephalometric metrics that were calculated based on a set of baseline cephalometric metrics; and determining an acceptable result of the surgery being planned based at least in part on the set of cephalometric metrics that are calculated.

6. A system for computer-assisted planning of a transplant surgery, comprising:

a memory storing instructions; and at least one processor coupled to the memory and executing the instructions to perform a method of computer-assisted planning of a transplant surgery, the method comprising:

creating a computer-readable representation of a donor skeletal fragment based on one or more medical imaging techniques, wherein the computer-readable representation of the donor skeletal fragment comprises one or more of: a vascular model or a neural model of the donor skeletal fragment;

creating a computer-readable representation of a recipient skeletal fragment based on one or more medical imaging techniques, wherein the computer-readable representation of the recipient skeletal fragment comprises one or more of: a vascular model or a neural model of the recipient skeletal fragment, wherein the computer-readable representation of the recipient skeletal fragment and the donor skeletal fragment comprises a segmented 3D reconstruction model that is created using the one or more medical imaging techniques and a segmentation algorithm, and wherein each voxel of the segmented 3D reconstruction model of the recipient skeletal fragment and the donor skeletal fragment comprises an associated anatomical attribute that classifies an anatomy for which each voxel represents;

determining one or more surgical cutting planes on the computer-readable representation of the donor skeletal fragment from which a portion of the donor skeletal fragment from the computer-readable representation of the donor skeletal fragment will be harvested;

determining one or more virtual cutting guides based on the one or more surgical cutting planes to be attached to the computer-readable representation of the donor skeletal fragment;

performing a virtual osteotomy to separate the portion of the donor skeletal fragment from the computer-readable representation of the donor skeletal fragment from a remainder portion of the donor skeletal fragment based on a position of the one or more virtual cutting guides that are attached to the computer-readable representation of the donor skeletal fragment;

positioning the donor skeletal fragment within a transplant region of the recipient skeletal fragment;

creating a hybrid computer-readable representation comprising the recipient skeletal fragment and the portion of the donor skeletal fragment during or after the positioning; and providing the hybrid computer-readable representation as an output.

7. A system for computer-assisted planning of a transplant surgery, comprising:

a memory storing instructions; and at least one processor coupled to the memory and executing the instructions to perform a method of computer-assisted planning of a transplant surgery, the method comprising:

obtaining a computer-readable representation of a donor skeletal fragment;

obtaining a computer-readable representation of a recipient skeletal fragment;

determining one or more surgical cutting planes on the computer-readable representation of the donor skeletal fragment from which a portion of the donor skeletal fragment from the computer-readable representation of the donor skeletal fragment will be harvested;

determining one or more virtual cutting guides based on the one or more surgical cutting planes to be attached to the computer-readable representation of the donor skeletal fragment;

performing a virtual osteotomy to separate the portion of the donor skeletal fragment from the computer-readable representation of the donor skeletal fragment from a remainder portion of the donor skeletal fragment based on a position of the one or more virtual cutting guides that are attached to the computer-readable representation of the donor skeletal fragment;

positioning the donor skeletal fragment within a transplant region of the recipient skeletal fragment;

creating a hybrid computer-readable representation comprising the recipient skeletal fragment and the portion of the donor skeletal fragment during or after the positioning;

tracking movement of the donor skeletal fragment of the computer-readable representation during the positioning; and updating the hybrid computer-readable representation based on the movement being tracked.

8. The system of claim 7, wherein the at least one processor is further operable to execute the method comprising:

identifying a set of cephalometric landmarks associated with the hybrid computer-readable representation;

calculating a set of cephalometric metrics for the set of cephalometric landmarks that are identified; and determining an acceptable result of the surgery being planned based at least in part on the set of cephalometric metrics that are calculated.

9. A system for computer-assisted planning of a transplant surgery, comprising:

a memory storing instructions; and at least one processor coupled to the memory and executing the instructions to perform a method of computer-assisted planning of a transplant surgery, the method comprising:

obtaining a computer-readable representation of a donor skeletal fragment;

obtaining a computer-readable representation of a recipient skeletal fragment;

determining one or more surgical cutting planes on the computer-readable representation of the donor skeletal fragment from which a portion of the donor skeletal fragment from the computer-readable representation of the donor skeletal fragment will be harvested;

determining one or more virtual cutting guides based on the one or more surgical cutting planes to be attached to the computer-readable representation of the donor skeletal fragment;

performing a virtual osteotomy to separate the portion of the donor skeletal fragment from the computer-readable representation of the donor skeletal fragment from a remainder portion of the donor skeletal fragment based on a position of the one or more virtual cutting guides that are attached to the computer-readable representation of the donor skeletal fragment;

positioning the donor skeletal fragment within a transplant region of the recipient skeletal fragment;

creating a hybrid computer-readable representation comprising the recipient skeletal fragment and the portion of the donor skeletal fragment during or after the positioning;

providing the hybrid computer-readable representation as an output;

identifying a set of cephalometric landmarks associated with the hybrid computer-readable representation, wherein the set of cephalometric landmarks comprise one or more of: Gonion ("Go"), Nasion ("N"), A point ("A"), B point ("B"), Sella ("S"), Menton ("M"), left/right Zygoma ("ZY"), Os occipital ("OCC");

calculating a set of cephalometric metrics for the set of cephalometric landmarks that are identified; and determining an acceptable result of the surgery being planned based at least in part on the set of cephalometric metrics that are calculated.

10. A system for computer-assisted planning of a transplant surgery comprising;

a memory storing instructions; and at least one processor coupled to the memory and executing the instructions to perform a method of computer-assisted planning of a transplant surgery, the method comprising:

obtaining a computer-readable representation of a donor skeletal fragment;

obtaining a computer-readable representation of a recipient skeletal fragment;

determining one or more surgical cutting planes on the computer-readable representation of the donor skeletal fragment from which a portion of the donor skeletal fragment from the computer-readable representation of the donor skeletal fragment will be harvested;

determining one or more virtual cutting guides based on the one or more surgical cutting planes to be attached to the computer-readable representation of the donor skeletal fragment;

performing a virtual osteotomy to separate the portion of the donor skeletal fragment from the computer-readable representation of the donor skeletal fragment from a remainder portion of the donor skeletal fragment based on a position of the one or more virtual cutting guides that are attached to the computer-readable representation of the donor skeletal fragment;

positioning the donor skeletal fragment within a transplant region of the recipient skeletal fragment;

creating a hybrid computer-readable representation comprising the recipient skeletal fragment and the portion of the donor skeletal fragment during or after the positioning;

providing the hybrid computer-readable representation as an output;

identifying a set of cephalometric landmarks associated with the hybrid computer-readable representation;

calculating a set of cephalometric metrics for the set of cephalometric landmarks that are identified;

determining an acceptable result of the surgery being planned based at least in part on the set of cephalometric metrics that are calculated; and, updating at least one of the one or more surgical cutting planes or cutting guides based on determining the acceptable result.

11. A system for computer-assisted planning of a transplant surgery comprising;

a memory storing instructions; and at least one processor coupled to the memory and executing the instructions to perform a method of computer-assisted planning of a transplant surgery, the method comprising:

obtaining a computer-readable representation of a donor skeletal fragment;

obtaining a computer-readable representation of a recipient skeletal fragment;

determining one or more surgical cutting planes on the computer-readable representation of the donor skeletal fragment from which a portion of the donor skeletal fragment from the computer-readable representation of the donor skeletal fragment will be harvested;

determining one or more virtual cutting guides based on the one or more surgical cutting planes to be attached to the computer-readable representation of the donor skeletal fragment;

performing a virtual osteotomy to separate the portion of the donor skeletal fragment from the computer-readable representation of the donor skeletal fragment from a remainder portion of the donor skeletal fragment based on a position of the one or more virtual cutting guides that are attached to the computer-readable representation of the donor skeletal fragment;

positioning the donor skeletal fragment within a transplant region of the recipient skeletal fragment;

creating a hybrid computer-readable representation comprising the recipient skeletal fragment and the portion of the donor skeletal fragment during or after the positioning;

providing the hybrid computer-readable representation as an output;

identifying a set of cephalometric landmarks associated with the hybrid computer-readable representation;

calculating a set of cephalometric metrics for the set of cephalometric landmarks that are identified;

determining an acceptable result of the surgery being planned based at least in part on the set of cephalometric metrics that are calculated;

determining an acceptable result of the surgery being planned based at least in part on the set of cephalometric metrics that are calculated; and comparing the set of cephalometric metrics that were calculated based on a set of baseline cephalometric metrics.

12. A non-transitory computer-readable medium including instructions to perform a method for computer-assisted planning of a transplant surgery, the method comprising:

creating a computer-readable representation of a donor skeletal fragment based on one or more medical imaging techniques, wherein the computer-readable representation of the donor skeletal fragment comprises one or more of: a vascular model or a neural model of the donor skeletal fragment;

creating a computer-readable representation of a recipient skeletal fragment based on one or more medical imaging techniques, wherein the computer-readable representation of the recipient skeletal fragment comprises one or more of: a vascular model or a neural model of the recipient skeletal fragment, wherein the computer-readable representation of the recipient skeletal fragment and the donor skeletal fragment comprises a segmented 3D reconstruction model that is created using the one or more medical imaging techniques and a segmentation algorithm, and wherein each voxel of the segmented 3D reconstruction model of the recipient skeletal fragment and the donor skeletal fragment comprises an associated anatomical attribute that classifies an anatomy for which each voxel represents;

determining one or more surgical cutting planes on the computer-readable representation of the donor skeletal fragment from which a portion of the donor skeletal fragment from the computer-readable representation of the donor skeletal fragment will be harvested;

determining one or more virtual cutting guides based on the one or more surgical cutting planes to be attached to the computer-readable representation of the donor skeletal fragment;

performing a virtual osteotomy to separate the portion of the donor skeletal fragment from the computer-readable representation of the donor skeletal fragment from a remainder portion of the donor skeletal fragment based on a position of the one or more virtual cutting guides that are attached to the computer-readable representation of the donor skeletal fragment;

positioning the donor skeletal fragment within a transplant region of the recipient skeletal fragment;

creating a hybrid computer-readable representation comprising the recipient skeletal fragment and the portion of the donor skeletal fragment during or after the positioning; and providing the hybrid computer-readable representation as an output.

13. A system for computer-assisted planning of a transplant surgery, comprising:

a memory storing instructions; and at least one processor coupled to the memory and executing the instructions to perform a method of computer-assisted planning of a transplant surgery, the method comprising:

obtaining a computer-readable representation of a donor skeletal fragment;

obtaining a computer-readable representation of a recipient skeletal fragment;

determining one or more surgical cutting planes on the computer-readable representation of the donor skeletal fragment from which a portion of the donor skeletal fragment from the computer-readable representation of the donor skeletal fragment will be harvested;

determining one or more virtual cutting guides based on the one or more surgical cutting planes to be attached to the computer-readable representation of the donor skeletal fragment;

performing a virtual osteotomy to separate the portion of the donor skeletal fragment from the computer-readable representation of the donor skeletal fragment from a remainder portion of the donor skeletal fragment based on a position of the one or more virtual cutting guides that are attached to the computer-readable representation of the donor skeletal fragment;

positioning the donor skeletal fragment within a transplant region of the recipient skeletal fragment;

creating a hybrid computer-readable representation comprising the recipient skeletal fragment and the portion of the donor skeletal fragment during or after the positioning;

tracking movement of the donor skeletal fragment of the computer-readable representation during the positioning;

updating the hybrid computer-readable representation based on the movement being tracked; and providing the hybrid computer-readable representation as an output.

* * * * *